US009978586B2

(12) United States Patent
Routh, Jr. et al.

(10) Patent No.: US 9,978,586 B2
(45) Date of Patent: May 22, 2018

(54) METHOD OF MATERIAL DEPOSITION

(71) Applicant: FEI Company, Hillsboro, OR (US)

(72) Inventors: Brian Roberts Routh, Jr., Beaverton, OR (US); Thomas G. Miller, Portland, OR (US); Chad Rue, Portland, OR (US); Noel Thomas Franco, Hillsboro, OR (US)

(73) Assignee: FEI Company, Hillsboro, OR (US)

( * ) Notice: Subject to any disclaimer, the term of this patent is extended or adjusted under 35 U.S.C. 154(b) by 0 days. days.

(21) Appl. No.: 15/087,968

(22) Filed: Mar. 31, 2016

(65) Prior Publication Data

US 2017/0133220 A1 May 11, 2017

Related U.S. Application Data

(60) Provisional application No. 62/252,308, filed on Nov. 6, 2015.

(51) Int. Cl.
| | |
|---|---|
| *H01L 21/00* | (2006.01) |
| *H01L 21/02* | (2006.01) |
| *C23C 14/22* | (2006.01) |
| *G01N 1/32* | (2006.01) |
| *H01J 37/305* | (2006.01) |
| *C23C 14/30* | (2006.01) |

(52) U.S. Cl.
CPC ...... *H01L 21/02266* (2013.01); *C23C 14/221* (2013.01); *G01N 1/32* (2013.01); *H01J 37/3056* (2013.01); *H01L 21/02164* (2013.01); *H01L 21/02362* (2013.01); *C23C 14/30* (2013.01); *H01J 2237/3174* (2013.01); *H01J 2237/31744* (2013.01); *H01J 2237/31745* (2013.01); *H01J 2237/31749* (2013.01); *H01L 21/02214* (2013.01)

(58) Field of Classification Search
CPC ........ H01L 21/02266; H01L 21/02214; H01L 21/02164; H01L 21/02362; C23C 14/221; C23C 14/30; H01J 2237/31749; H01J 2237/3174; H01J 2237/31744; H01J 2237/31745; H01J 37/3053
See application file for complete search history.

(56) References Cited

U.S. PATENT DOCUMENTS

| | | | |
|---|---|---|---|
| 5,435,850 A | 7/1995 | Rasmussen | |
| 5,851,413 A | 12/1998 | Casella et al. | |
| 2013/0319849 A1 | 12/2013 | Fuller et al. | |
| 2014/0190934 A1* | 7/2014 | Schmidt | ................ G01N 1/286 216/37 |
| 2014/0302252 A1 | 10/2014 | Mulders et al. | |
| 2014/0357088 A1 | 12/2014 | Rue et al. | |
| 2015/0348752 A1 | 12/2015 | Foord et al. | |
| 2016/0035540 A1* | 2/2016 | Kruger | ................ G01N 1/286 250/440.11 |

* cited by examiner

*Primary Examiner* — Kimberly Rizkallah
*Assistant Examiner* — Alexander Belousov
(74) *Attorney, Agent, or Firm* — Scheinberg & Associates, PC; Michael O. Scheinberg

(57) ABSTRACT

A method and apparatus for material deposition onto a sample to form a protective layer composed of at least two materials that have been formulated and arranged according to the material properties of the sample.

16 Claims, 17 Drawing Sheets

METHOD OF MATERIAL DEPOSITION

TECHNICAL FIELD OF THE INVENTION

The present invention relates to charged particle beam induced deposition, and more particularly to precursor gas composition for FIB and SEM beam chemistry.

BACKGROUND OF THE INVENTION

In the prior art, it is known to deposit material onto a sample via ion beam induced deposition (IBID), typically performed in a focused ion beam (FIB) instrument, and electron beam induced deposition (EBID), usually performed in a scanning electron microscope (SEM) instrument. According to known methods, a sample is placed in an evacuable specimen chamber of a charged particle beam apparatus—typically either a FIB system or a SEM system. The charged particle (or other) beam is applied to the sample surface in the presence of a deposition gas, often referred to as a precursor gas. A layer of the precursor gas adsorbs to the surface of the sample. The thickness of the layer is governed by the balance of adsorption and desorption of the gas molecules on the sample surface, which in turn depends on, for example, the partial gas pressure, the substrate temperature, and the sticking coefficient. The thickness of the resultant layer can vary according to the application.

Material deposition can be performed with a variety of different gas precursors depending on the application. For example, tungsten hexacarbonyl ($W(CO)_6$) gas may be used to deposit tungsten and naphthalene gas may be used to deposit carbon. A precursor gas of TEOS, TMCTS, or HMCHS gas in combination with an oxidizer such as $H_2O$ or $O_2$ may be used to deposit silicon oxide ($SiO_x$). For deposition of platinum (Pt), a (methylcyclopentadienyl) trimethyl platinum gas may be used.

The material depositions obtained from these different precursors have different properties. For example, IBID Pt material deposited using (methylcyclopentadienyl) trimethyl platinum precursor tend to be "softer." That is, such softer materials are more susceptible to subsequent ion beam sputtering than "harder" IBID carbon or tungsten layers obtained with naphthalene or $W(CO)_6$, respectively. Silicon oxide layers using a precursor of TEOS, TMCTS, or HMCHS gas in combination an oxidizer such as $H_2O$ or $O_2$ tend to be more of a "medium" hardness. The relative "hardness" or "softness" of the material is dependent on the angle of incidence of the beam. In some material pairs the "harder" material becomes softer at a differing angle of incidence. Other differences exist as well. For example, when platinum films are used as sacrificial caps prior to FIB cross-sectioning (such as occurs in TEM preparation), the soft nature of the film tends to result in smooth cross-sectional cut face. By contrast, carbon films are extremely hard and tend to produce artifacts on the cut face known as "curtaining." In addition to hardness properties the growth rates of these different deposition precursors may also be a significant factor for various applications.

The following are examples of gas precursors of various classes. For example, class C etchants may include oxygen ($O_2$), nitrous oxide ($N_2O$), and water. Metal etchants may include iodine ($I_2$), bromine ($Br_2$), chlorine ($Cl_2$), xenon difluoride ($XeF_2$), and nitrogen dioxide ($NO_2$). Dielectric etchants may include xenon difluoride ($XeF_2$), nitrogen trifluoride ($NF_3$), trifluoroacetamide (TFA), and trifluoroacetic acid (TFAA). Metal deposition precursor gases may include (methylcyclopentadienyl) trimethyl platinum, tetrakis (triphenylphosphine) platinum (0), what is (0) tungsten hexacarbonyl ($W(CO)_6$), tungsten hexafluoride ($WF_6$), molybdenum hexacarbonyl ($Mo(CO)_6$), dimethyl (acetylacetonate) gold (III), tetraethylorsosilicate (TEOS), and tetraethylorsosilicate (TEOS) plus water ($H_2O$). Dielectric deposition precursors may include tetraethylorsosilicate (TEOS), tetraethylorsosilicate (TEOS) plus water ($H_2O$), hexamethylcyclohexacyloxane (($HMCHS$)+$O_2$), and tetramethylcyclotetrasiloxane (($TMCTS$)+$O_2$). Carbon deposition precursors may include naphthalene and dodecane ($C_{12}H_{26}$), and planar delayering agents may include methylnitroacetate. Although these are many examples of available gas precursors many others exist and are available for use.

Beam induced deposition is used in a wide variety of applications for depositing a material onto a target surface of a sample such as a semiconductor wafer. The materials are deposited for a variety of reasons such as to form thin-film surfaces, electrical connections, protective coatings for semiconductor feature characterization and analysis, and capping material for milling high-aspect ratio structures (such as vias). However, when there is a significant difference between the hardness of the sample and the deposited capping material, it can be difficult to obtain the desired structure, shape, and surface characteristics of a prepared sample. For example, it can be difficult to control sloped surfaces in the formation of milled structures, because the differential sputter rates of the materials can cause slope changes at the interface between the materials. Additionally, artifacts can occur on FIB milled surfaces during a cross-sectioning process for preparing samples for feature characterization and analysis.

Techniques using FIB systems are known for preparing ultra-thin samples for feature characterization and analysis in which it is important to minimize the occurrence of surface artifacts introduced during the milling process.

As semiconductor geometries continue to shrink, manufacturers increasingly rely on transmission electron microscopes (TEMs) for monitoring the manufacturing process, analyzing defects, and investigating interface layer morphology. Transmission electron microscopes allow observers to see features having sizes on the order of nanometers. In contrast to scanning electron microscopes (SEMs), which only image the surface of a material, TEMs also allow analysis of the internal structure of a sample. In a TEM, a broad beam impacts the sample and electrons that are transmitted through the sample are detected to form an image of the sample. A scanning transmission electron microscope (STEM) combines the principles of a TEM and SEM and can be performed on either instrument. The STEM technique scans a very finely focused beam of electrons across a sample in a raster pattern. The sample must be sufficiently thin to allow many of the electrons in the primary beam to travel through the sample and exit on the opposite side.

Because a sample must be very thin for viewing with transmission electron microscopy (whether TEM or STEM), preparation of the sample can be delicate, time-consuming work. The term "TEM" as used herein refers to a TEM or a STEM and references to preparing a sample for a TEM are understood to also include preparing a sample for viewing on a STEM. The term "STEM" as used herein also refers to both TEM and STEM.

There are several methods for preparing a thin sample for viewing with a TEM or STEM. Some methods entail extracting a sample without destroying the entire material from which the sample is extracted. Other methods require destroying the material to extract the sample. Some methods provide extraction of a thin sample referred to as a lamella. The lamella may require thinning before TEM or STEM viewing.

Lamella samples for TEM viewing are typically less than 100 nm thick, but for some applications samples must be considerably thinner. With advanced semiconductor manufacturing processes at design nodes of 30 nm and below, the sample needs to be less than 20 nm in thickness in order to avoid overlap among small scale structures. Some applications, such as analysis of next-node semiconductor devices, require lamellae having a thickness of 15 nm or less to isolate specific devices of interest. Current methods of thinning lamellae are difficult and not robust. Thickness variations in the sample result in sample bending or bowing, overmilling, or other catastrophic defects that may destroy the lamella. For such thin samples, preparation is a critical step in TEM analysis that significantly determines the quality of structural characterization and analysis of the smallest and most critical structures.

It is known to provide a protective layer deposited over the desired lamella location before thinning to protect the region of interest on the sample from exposure to the ion beam and to prevent bending or bowing. In one commonly used preparation technique as seen in FIGS. 1-3, a protective layer 22 of a material such as tungsten, carbon, or platinum is first deposited over the area of interest on a top surface 23 of a sample body as shown in FIG. 1 using electron beam or ion beam deposition. Next, as shown in FIGS. 2 and 3, a focused ion beam using a high beam current with a correspondingly large beam size is used to mill large amounts of material away from the front and back portion of the region of interest. The remaining material between the two milled areas 24 and 25 forming a thin vertical sample section 26 that includes an area of interest. Typically, the area of interest is contained in the top 200-300 nm below the sample surface. The area 25 milled on the back side of the region of interest is shown smaller that the front area 24. The smaller milled area 25 is basically to save time, but also prevents the finished sample from falling over into larger milled area 24 making it difficult to remove the sample section 26 from the sample body. Sample section 26 may then be cut away from the sample body using a focused ion beam and then lifted out using, for example, a micromanipulator, in a well-known manner. The sample section 26 is then typically transferred to a TEM grid and thinned. The sample section 26 may then be analyzed using a TEM or other analytical tools.

Significant problems occur in the preparation of ultra-thin (<30 nm thick) TEM samples. For example, a protective layer of platinum over the area of interest is too soft and often fails during lamella thinning, becoming completely consumed by peripheral erosion from the ion beam tails before the lamella thinning is complete. Layers of harder materials may resist erosion better than softer materials, but may cause undesirable artifacts on the cross-sectional face of the lamella.

FIGS. 4 and 5 show examples of problems in the preparation of ultra-thin samples. As seen in FIG. 4, a cross-section of a lamella sample 30 is shown prepared with a soft Pt cap 32 deposited on a hard diamond substrate 34. When the lamella 30 is prepared by thinning to the required thickness dimension, this hardness mismatch results in faster erosion of the softer Pt cap 32 than the harder diamond substrate 34. This combination would prevent the user from thinning the lamella as much as desired, because the protective cap 32 would eventually be completely consumed before the substrate 34 was adequately thinned. Conversely, as seen in FIG. 5, a cross-section of a lamella sample 36 is shown prepared with a hard carbon cap 38 placed on a soft copper substrate 40. In this example, undercutting 42 may be observed because the softer substrate 40 is consumed faster than the harder cap 38. This can lead to premature failure of the lamella, as well as cross-sectioning surface artifacts, such as "curtaining."

Curtaining is an artifact that causes the surface of a sample to be rippled or uneven. Curtaining may arise for a variety of reasons. If the sample is non-homogeneous, consisting of different materials with different sputter rates, then the harder materials may form resistant areas that project slightly from the cross-sectional face. These projections shield regions below them, leading to vertical streaks that propogate downwards. FIG. 6 shows a sample 44 having a silicon substrate with a tungsten protective layer exhibiting curtaining. The "curtains" arise because the tungsten is harder or more resistant to sputtering from the ion beam than the silicon substrate. This leads to features that protrude slightly from the cross-sectional face of the substrate. The harder, overhanging tungsten basically shields the substrate directly below it leaving vertical projections of the tungsten. Alternatively, some hard capping materials form ripple-like or rectilinear patterns when exposed to the ion beam, even though the capping material is itself internally homogenious. FIG. 7 shows a sample 46 having a silicon substrate with a carbon protective layer exhibiting curtaining. When a cross-sectional mill is performed, the carbon layer material gradually assumes a highly textured surface. Thus, the topography of the carbon layer leads to curtaining in this example. Top-down thinning of a sample having these types of structural or density variations will cause vertical ridges or variations to propagate from the denser materials (i.e., metal lines) near the top of the sample (the top being defined as closest to the ion beam source) down the face of the cross-section, running in a direction parallel to the ion beam direction. Curtaining is most often observed in semiconductor materials where multiple patterned layers of materials having a low sputtering yield blocks a faster sputtering yield material. Curtaining may also be observed in materials exhibiting different topographic regions where changes in sputtering yields vary with the milling incident angle. Samples with voids also induce curtains. Curtaining artifacts reduce the quality of the TEM imaging and limit the minimal useful specimen thickness.

Another type of artifact is referred to as a "golf tee." For example, a layer of either tungsten or carbon on top of a region of interest on a sample, which is typically a material such as silicon. The capping material and the silicon substrate have different "hardnesses," (resistance to sputtering from the ion beam) resulting in a top-to-bottom thickness variation called a "golf-tee", wherein the sample is thicker at the top and narrows to a thinner dimension so that the sample has a "golf tee" profile when observed in a Y-section. Since the region of interest is usually contained near the top surface of the lamella the thicker dimension can obscure the region of interest and cause a less than desirable sample for TEM viewing.

An example of a "golf-tee" effect can be seen in FIG. 8, which shows a TEM sample 50 with an ion beam induced deposition (IBID) tungsten protective layer 52 located on the top surface of sample 50. In this example, after thinning the sample 50 is 44 nm wide directly under protective layer 52 and narrows to 25 nm wide at 150 nm below protective layer 52. This thickness variation is the result of the differential etch rate between the silicon substrate and the tungsten protective layer. Tungsten is a harder, denser material than silicon and has a significantly lower etch rate, which causes the tungsten protective layer 52 to be wider than the lamella body. Typically, the region of interest is located in the general area where the "golf-tee" occurs obscuring or interfering with the region of interest for TEM viewing.

What is needed is an improved method of material deposition to obtain a controlled work piece surface that is free of surface artifacts and slope changes.

SUMMARY OF THE INVENTION

It is an object of the invention to provide an improved method of material deposition that combines the properties of at least two precursors for reducing surface artifacts and slope changes.

In accordance with one preferred embodiment, a material deposition is carried out to provide a protective material layer having a sputter rate that substantially matches the sputter rate of the substrate material. A charged particle beam is directed toward the substrate in a vacuum chamber of a FIB system to induce material deposition from a precursor gas mixture. Resistance to sputtering of the protective layer material deposition can be adjusted by changing the ratio of the gas mixture components. A multiple gas injecting system is used having variable flow control and mixing capabilities that can vary the precursor ratios over a wide range to vary the hardness of the protective layer material depending on the material of the sample substrate.

In accordance with another preferred embodiment, material deposition is carried out to provide a protective layer that includes two or more material compositions deposited in layers with each layer having different etch rates. Preferably, a charged particle beam is directed toward the substrate in a vacuum chamber of a FIB system to induce deposition from a precursor gas of a first protective layer onto the sample substrate above the region of interest. An ion beam is then directed toward the sample substrate to induce deposition from a precursor gas of at least a second protective layer on top of the first protective layer. Preferably, the first protective layer has an etch rate that closely matches the etch rate of the sample and the second protective layer (and any further layers) has an etch rate that is different than the etch rate of the sample. For example, for a softer substrate, a softer protective material may be first deposited to be in direct contact with the substrate and then a second harder layer may be deposited on top of the first layer. The harder layer will resist erosion from the ion beam while the softer bottom layer will prevent cross-sectioning artifacts. A bottom layer that has a sputter rate that closely matches the sputter rate of the substrate lessens the risk of cross-sectioning artifacts. For harder substrates such as diamond, carbon, or silicon carbide, a harder protective layer may be first deposited to be in direct contact with the substrate with a softer material layer deposited on top of the first layer.

In another preferred embodiment, material deposition is carried out to provide alternating layers of material to form the protective layer in which the etch rate of the protective layer material is "tuned" by depositing the alternating, thin layers of material using discrete gas chemistries, which forms an alternating "parfait-like" macrostructure with an etch rate that is between the etch rates of the individual components. By adjusting the thickness of the individual components, as well as the total number of layers, the user may achieve some degree of tunability, to achieve the desired film property. A limiting extreme of infinite ultrathin alternating layers could be deposited resulting in a deposition resembling a composite mix.

In another preferred embodiment, a mixture of gas precursors is used in material deposition, but the ratio of the gases is gradually adjusted during the course of the deposition to create a composite capping material, such that the bottom of the protective layer is mostly one component and the top of the layer is mostly another component, with intermediate regions having intermediate compositions. This provides a gradual transition from hard to soft (or vice-versa), as the mill progresses through the protective material.

In another preferred embodiment, the material deposition methods described herein may be performed with TEM lamella preparation for tuning the hardness of the sacrificial protective cap to prevent lamella failure due to erosion from the beam tails, and can minimize cross-sectioning artifacts such as curtaining and sidewall slope changes at interfaces.

In yet another preferred embodiment, the material deposition methods described herein may be performed with applications in which a composite capping layer is used to create single-sided FIB cross-section in general, with a cut face that is free of defects and slope changes.

In still another preferred embodiment, the material deposition methods described herein may be performed with applications in which composition deposition films can be used to control the milled profile of high-aspect ratio structures (such as vias) that are created with ion beam milling.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the scope of the invention as set forth in the appended claims.

DETAILED DESCRIPTION OF PREFERRED EMBODIMENTS

Embodiments of the invention provide a method for improved method of material deposition onto a work piece that combines the properties of at least two precursors for reducing surface artifacts and slope changes.

According to a first preferred embodiment of the present invention, a substrate, such as a semiconductor wafer, is loaded into a dual-beam FIB/SEM system having both a FIB column and a SEM column. Although a dual-beam system is discussed it is to be understood that other FIB systems may be used to carry out the invention. Wafers may be transferred manually or are preferably transferred by way of a multi-wafer carrier and auto-loading robot (not shown).

In applications for preparing lamella samples the location of a region on the sample containing a feature of interest for extraction and analysis (i.e., the lamella site) is determined. For example, the substrate may be a semiconductor wafer or portion thereof and the sample to be extracted may include a portion of an integrated circuit that is to be observed using the TEM. Typically, the substrate is coarsely aligned by using machine vision to locate reference marks on the wafer or wafer piece, or using the edges and alignment notch or flat of an unpatterned wafer. Alternately, a lamella site may be located automatically using image recognition software. Suitable image recognition software is available from Cognex Corporation of Natick, Mass. Image recognition software can be "trained" to locate the desired lamella locations by using sample images of similar features or by using geometric information from CAD data. Automated FIB or SEM metrology can also be used to identify or help identify the lamella site. Metrology may consist of image-based pattern recognition, edge finding, ADR, center-of-mass calculations, or blobs. If desired, fiducial marks may be milled into the substrate surface as a precise and accurate locating mark.

A composite protective layer is then deposited over the lamella site to protect the sample. In a first preferred embodiment, an IBID or EBID deposition can be performed using a multiple gas injection system in which two or more precursor gases flow simultaneously. For example, a deposition may be performed in which the deposited material has properties intermediate to the two individual components. For example, an IBID deposition obtained with mixtures of Pt and C precursors may be performed to obtain a protective layer having properties intermediate between the properties obtained with the Pt and C precursors individually. Precursor mixing can be performed in numerous ways. For example, a single gas nozzle outlet can be shared by two or more vessels containing individual chemical precursors, and the relative flow rates of the individual components can be controlled by pulsed valves situated between the chemical precursor container and the outlet.

Figure 1:
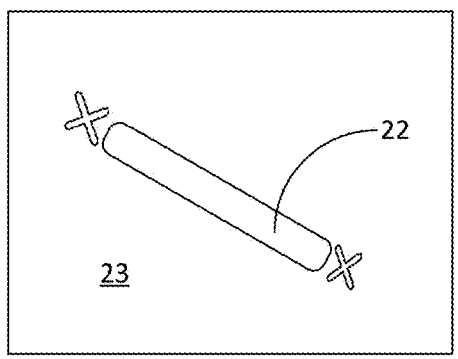
FIGS. 1-3 illustrate the steps in an ex-situ sample preparation technique according to the prior art.
Figure 2:
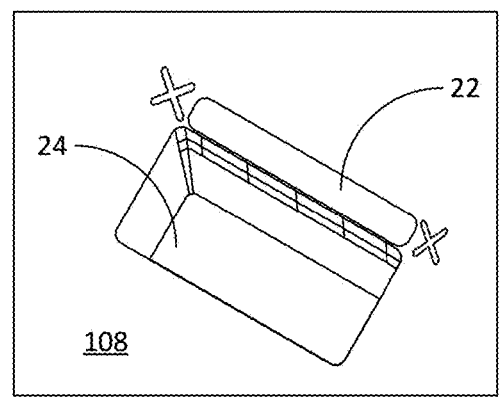
Figure 3:
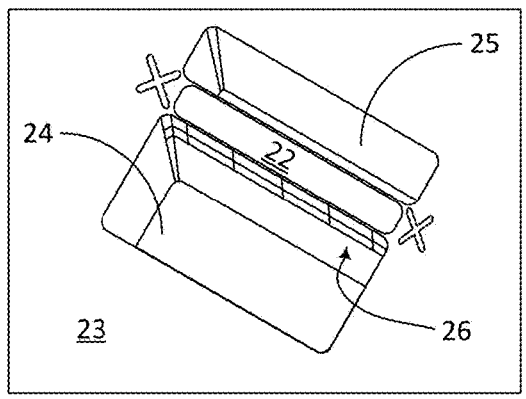
Figure 4:
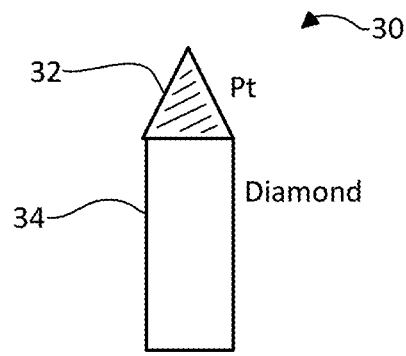
FIG. 4 shows a prior art lamella profile having a hard diamond substrate and an easily consumable soft platinum top layer.
Figure 5:
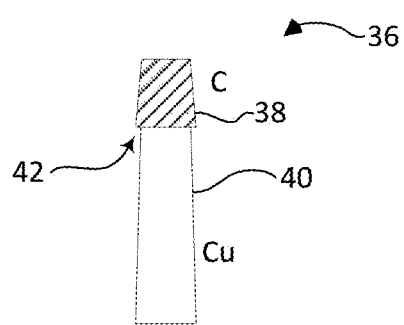
FIG. 5 shows a prior art lamella profile having a soft copper substrate and hard carbon top layer with resulting undercutting.
Figure 6:
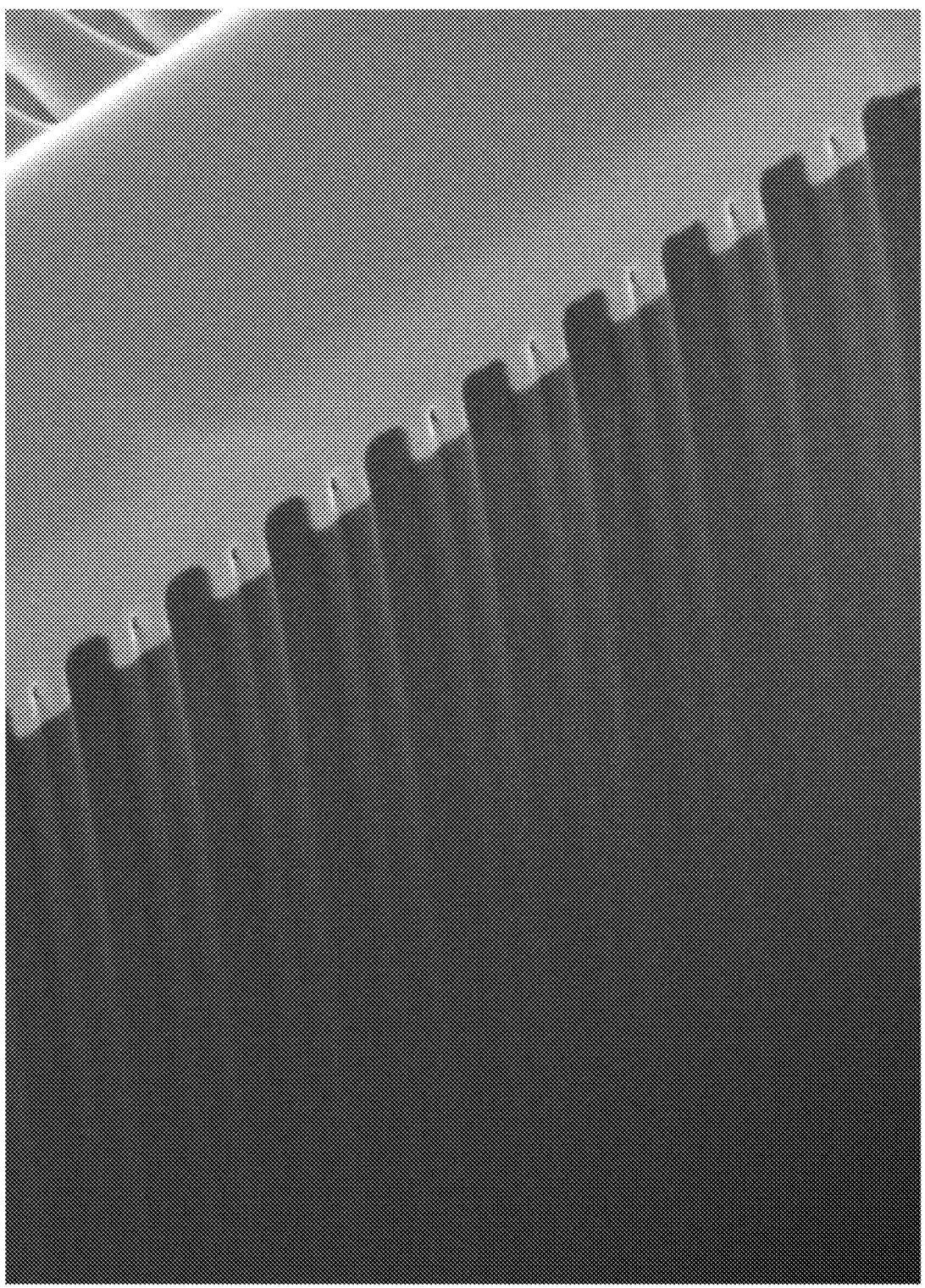
FIG. 6 is a photomicrograph of a FIB cross-sectional face with a tungsten top layer showing curtaining according to the prior art.
Figure 7:
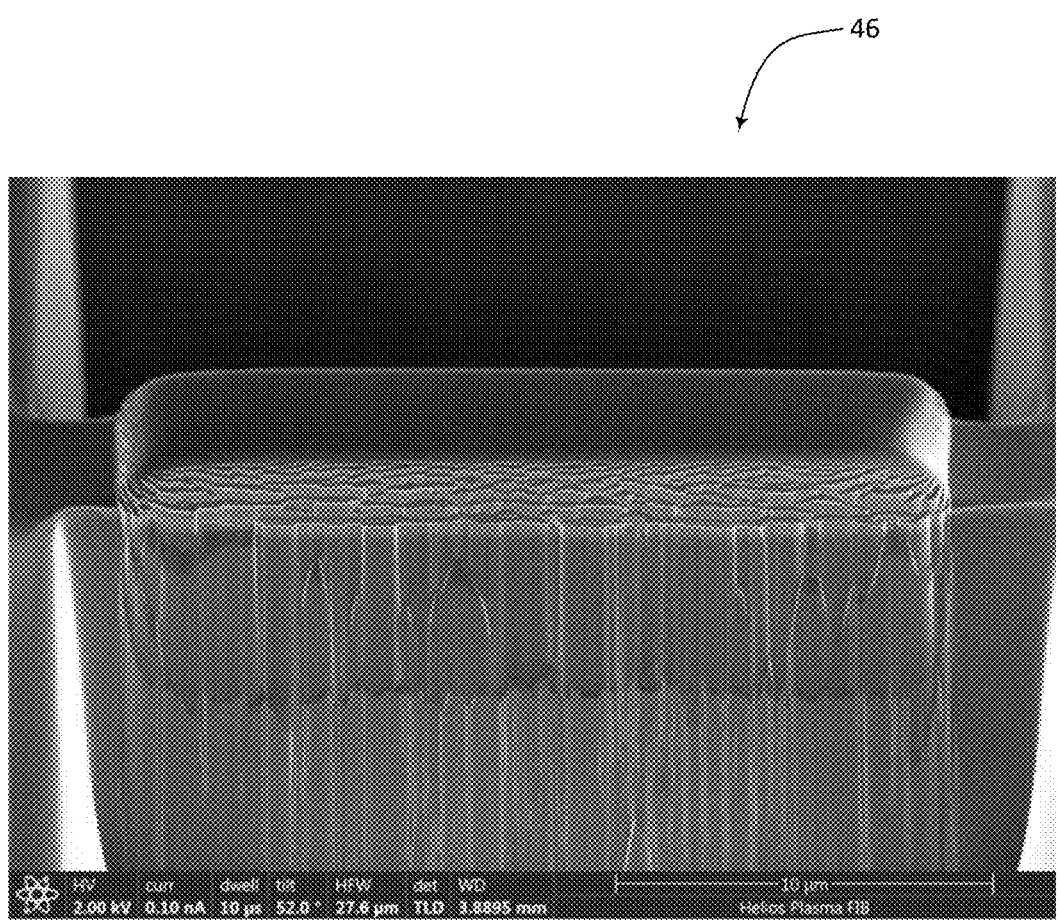
FIG. 7 is a photomicrograph of a thinned TEM sample with a carbon top layer showing curtaining according to the prior art.
Figure 8:
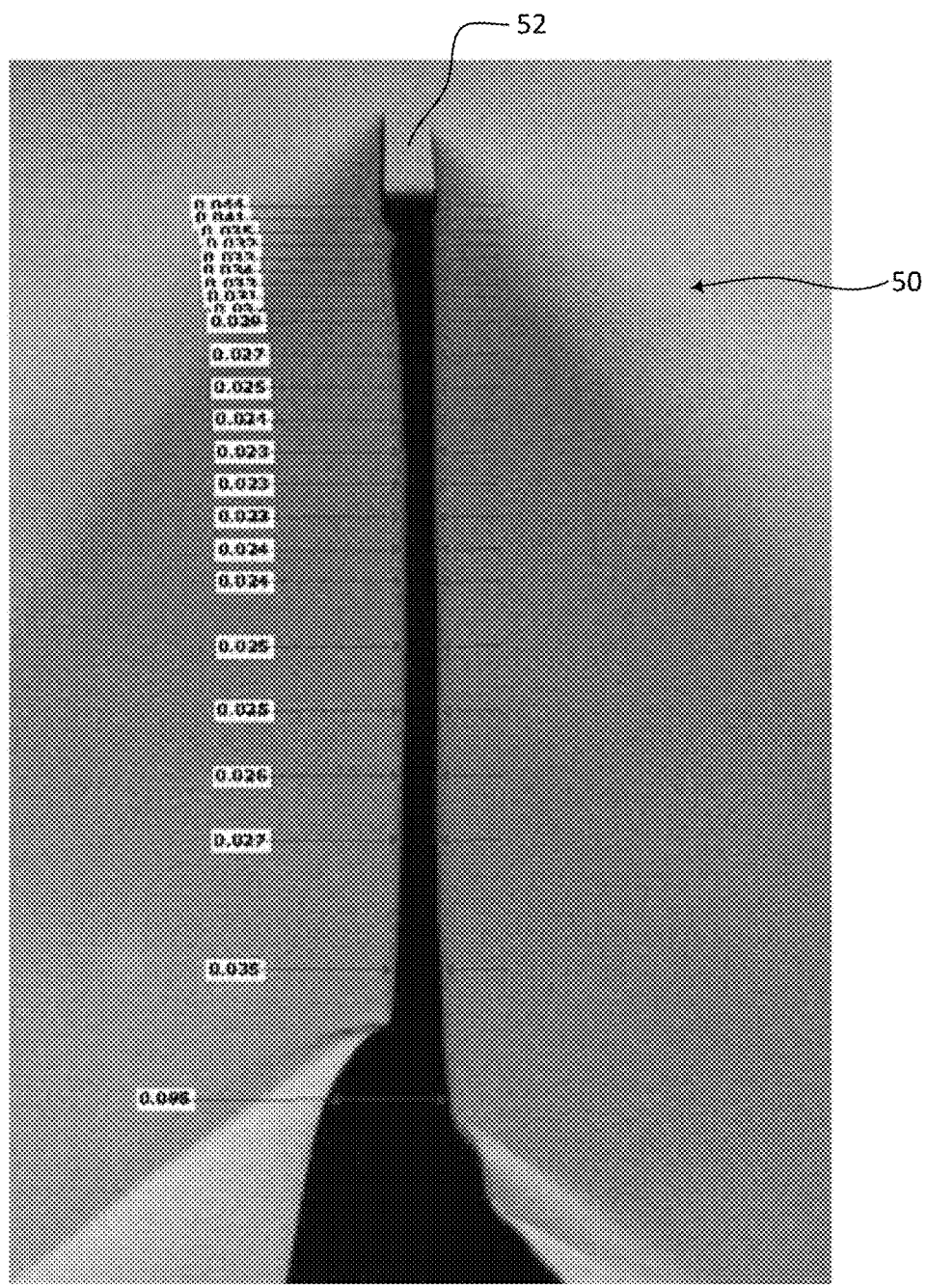
FIG. 8 shows an image of a lamella after thinning with a "golf-tee" artifact according to the prior art.
Figure 9:
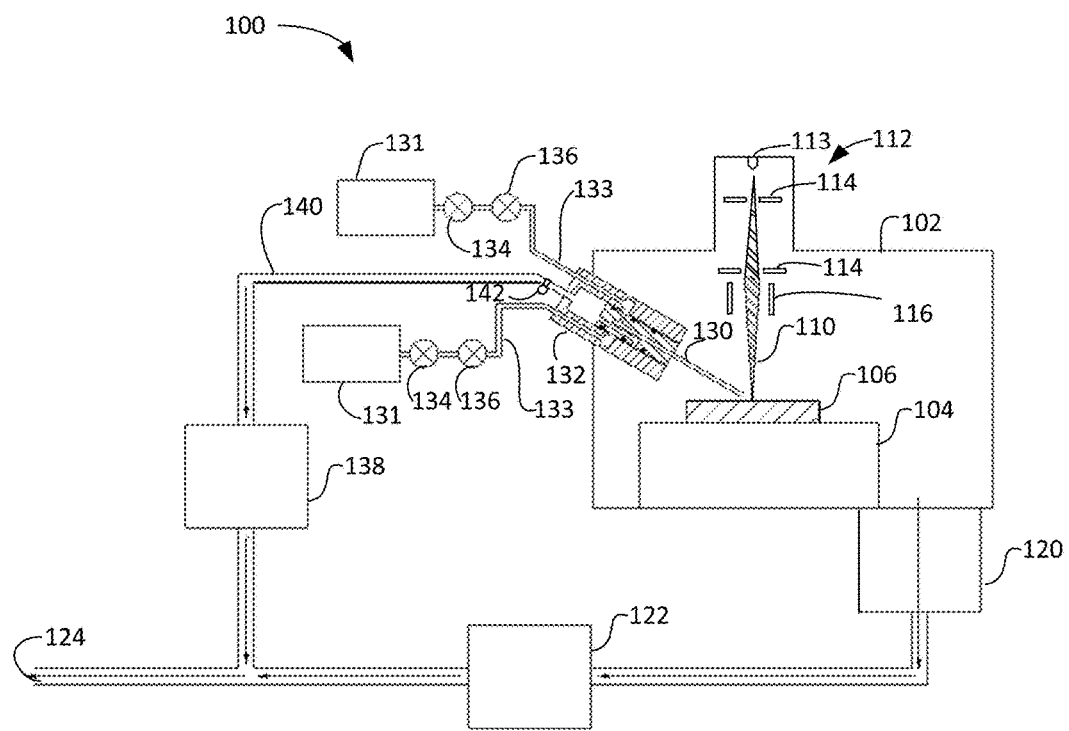
FIG. 9 shows schematically a charged particle beam system with a multigas injection system (MGIS).

FIG. 9 shows a schematic of a beam system 100 incorporating an embodiment of the invention. Beam system 100 includes a sample vacuum chamber 102 containing a sample stage 104 for supporting a work piece 106 to be processed by a beam 110, which is produced by a beam producing subsystem, such as a laser or a charged particle beam column. For example, a charged particle beam column 112 includes a charged particle source 113, one or more focusing lenses 114, and a deflector 116 for scanning or otherwise directing the beam 110 in a designated pattern on the work piece surface. An evacuation system, such as a combination of a high vacuum turbo pump 120 and a backing pump 122, maintains a vacuum of preferably less than $10^{-3}$ mbar more preferably less than $10^{-4}$ mbar, and even more preferably less than or equal to about $10^{-5}$ mbar in sample vacuum chamber 102 during processing. Backing pump 122 exhausts to an exhaust outlet 124.

Gas is supplied to a local area at the work piece surface by a retractable needle 130 that extends from a multiple gas injection system (MGIS) valve 132, which is described in more detail below. Gases, such as deposition precursor gases, etch precursor gases, or inert purge gases, are stored in gas reservoirs 131. The term "reservoir" is used broadly to include any gas source. Some of reservoirs 131 may include solid or liquid materials that are heated, for example, in a crucible, to evolve the desired gas, while other reservoirs 131 may include compressed gases. Each reservoir 131 is connected to MGIS valve 132 by a corresponding conduit 133, with a regulating valve 134 and a stop valve 136 in the flow path between each reservoir 131 and MGIS valve 132. While FIG. 9 shows two reservoirs with corresponding conduits, the invention is not limited to any number of reservoirs. Some embodiments of the invention use six or more reservoirs, while other embodiments may use a single gas source.

When a pre-set gas recipe is executed, the MGIS valve 132 needle 130 is extended and process gases flow from the valve 132 through needle 130 to the surface of work piece 106 near the point at which charged particle beam 110 is focused.

Sample stage 104 is used to position the work piece beneath the charged particle beam 110 and the needle 130. Gases from needle 130 in the sample vacuum chamber are eventually pumped from the chamber by a turbo pump 120. Vacuum pump 138 removes remaining gases from the interior of the MGIS valve through MGIS vacuum conduit 140, which is equipped with MGIS vacuum valve 142.

The specific recipe for the composite protective layer consists of mixing precursors in specific ratios depending on the material of the sample substrate. Preferably, one of the precursors will yield a relatively soft deposition material, and the other precursor will yield a relatively hard deposition material. Therefore, a user can tune the hardness of the deposition layer to be anything in between the properties of each individual precursor. The precursors are mixed in such a ratio to match the sputter rate of the protective layer material to the sputter rate of the substrate material to enable adequate thinning and to prevent interface artifacts. The duty cycles of the valves in the MGIS delivery hardware can be continuously varied between 0% and 100%. Therefore, a deposition material can be adjusted to have properties intermediate between those of the individual mixed precursor components. This allows customized deposition to different substrate materials and different applications.

Figure 10:
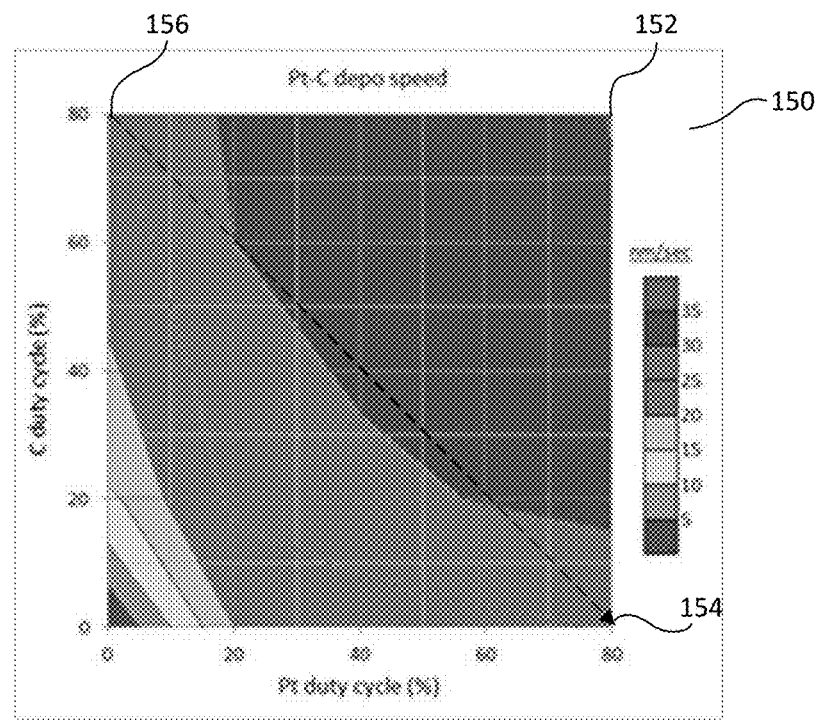
FIG. 10 shows a contour plot of vertical deposition growth rate as a function of the valve duty cycles for the Pt precursor (X axis) and C precursor (Y axis).
Figure 11:
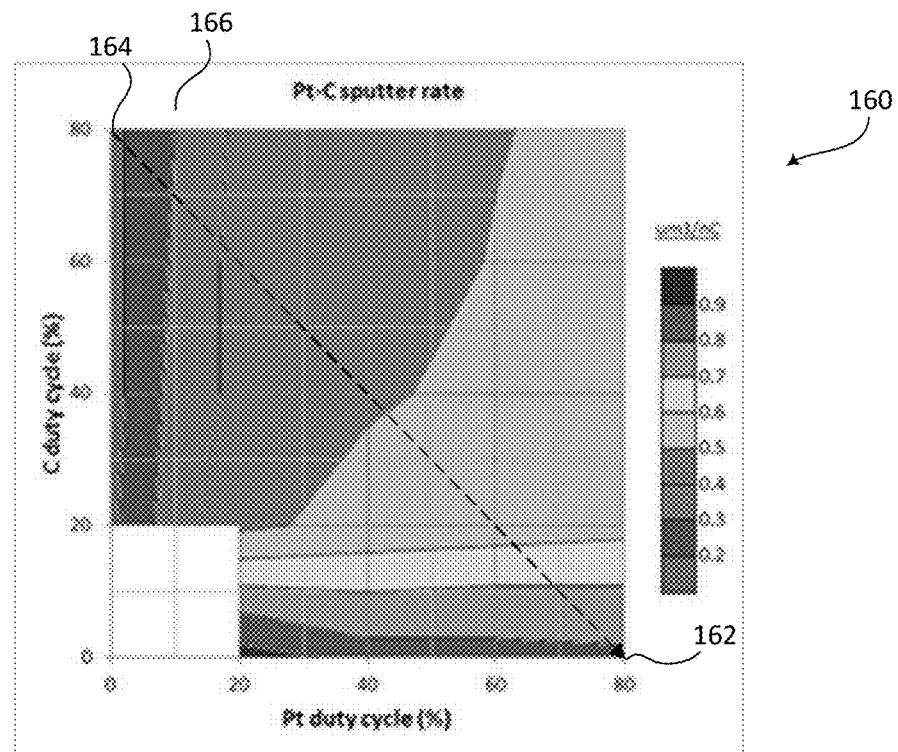
FIG. 11 shows a contour plot of sputter rates of deposited C-Pt composite materials as a function of valve duty cycles for the Pt precursor (X axis) and C precursor (Y axis).

In one example, a protective carbon-platinum (C—Pt) layer is deposited. The C—Pt precursors are mixed in a specific ratio depending on the material of the substrate. This is achieved by adjusting the C—Pt ratio, as indicated in the contour plots as seen in FIGS. 10 and 11. In FIG. 10, a contour plot 150 of vertical deposition growth rate (nm/sec) as a function of the valve duty cycles for the Pt precursor (X axis) and C precursor (Y axis) is shown. The highest growth rate is indicted by the green circle 152, and growth rates of standard single-precursor materials are indicated by the gray 154 and black 156 circles for Pt and C, respectively. In FIG. 11, a contour plot 160 of sputter rates of deposited C—Pt composite materials as a function of valve duty cycles for the Pt precursor (X axis) and C precursor (Y axis) is shown. The sputter rates of the standard single-precursor materials are indicated by the gray 162 and black 164 circles for Pt and C, respectively. Adding a small amount of Pt to a mostly C deposition, the conditions marked by the green circle 166, for example, results in a material that is superior as a protective cap layer than either individual component. The layer is much harder than Pt alone but does not have the curtaining effects of C alone. The variable duty cycle valve control, or percentage of "on" time of the pulsed valves, and mixing capability of the multiple gas injection system enables such adjustment. Thus, a desired "hardness" can be achieved by moving along the dotted line in FIG. 11. Therefore, a user may customize the hardness of the deposited layer to suit the sample, and especially to match the hardness of the sample substrate.

Figure 12:
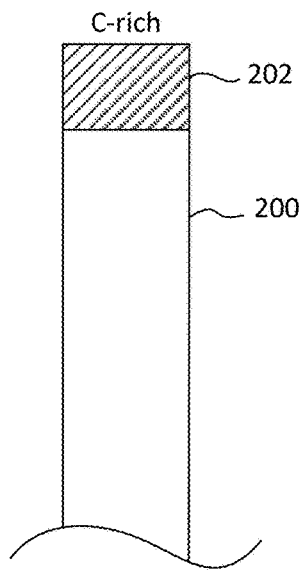
FIG. 12 shows a lamella profile with a C-rich protective composite layer.
Figure 13:
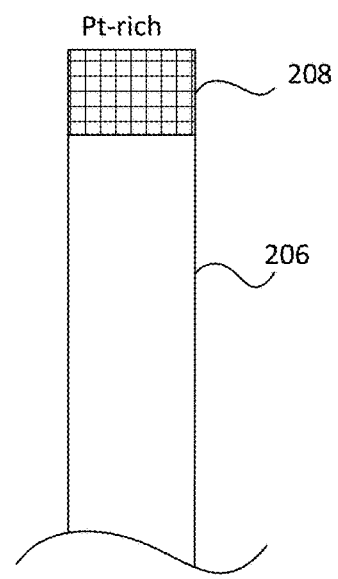
FIG. 13 shows a lamella profile with a Pt-rich protective composite layer.
Figure 14:
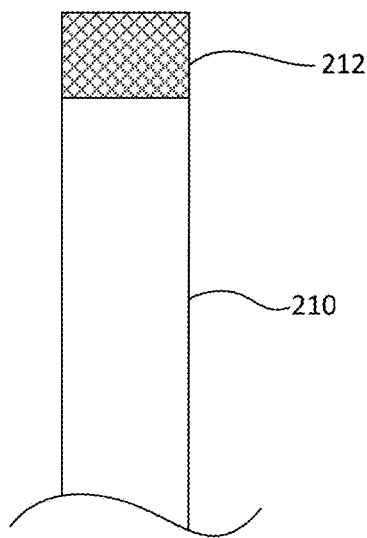
FIG. 14 shows a lamella profile with a C-Pt protective composite layer.

For example, as seen in FIGS. 12-14, a C—Pt composite material deposition having various hardness properties is carried out onto a substrate. For example, a C—Pt composite material can be formed onto a substrate 200 by continuously adjusting the valve duty cycle to achieve a C-rich composite (C valve duty cycle=80%, Pt valve duty cycle<2%), resulting in a very hard protective layer 202 (but not as hard as C alone) as seen in FIG. 12. As seen in FIG. 13, a C—Pt composite material can be formed onto a substrate 206 by continuously adjusting the valve duty cycle to achieve a Pt-rich composite (C valve duty cycle<2%, Pt valve duty cycle=80%), resulting in a very soft protective layer 208 (but not as soft as Pt alone). If a hard substrate sample is used, such as diamond, a C-rich layer having a hardness that closely matches the hardness of the diamond substrate may be deposited. As an example seen in FIG. 14, a substrate 210 having protective layer of C—Pt material 212 deposited with an MGIS setting of 80%-5% (C to Pt) is preferable to a layer obtained with either pure C or pure Pt precursors. An 80%-5% ratio has a higher material growth rate than individual C or Pt used alone. Additionally, this ratio has a higher sputter resistance than Pt and has fewer curtaining artifacts than C.

Other depositions may be obtained for substrates having various hardness properties. For example, a protective layer with intermediate duty cycles, (for example, 40% for both carbon and platinum), will have properties approximately intermediate to the properties obtained with either individual component. For samples with softer substrate properties, such as an organic resin, the deposition precursor may be adjusted to be Pt rich.

Possible duty cycle and sample combinations include a medium hard silicon substrate with a deposition layer using a valve duty cycle of 50%-50% (C to Pt), a hard diamond substrate with a deposition layer using a valve duty cycle of 80%-1% (C to Pt), and a soft resin substrate with a deposition layer using a valve duty cycle of 5%-80% (C to Pt). The precursors can be mixed with a conventional MGIS system as well in which the ratio of the precursors could be adjusted crudely by controlling the crucible temperature of each agent. However, many duty cycle combinations are possible and these examples illustrate that the hardness of the deposited material can be continuously varied to match the hardness of the substrate material.

In addition to the pulsed valve mixing strategy described above, other precursor delivery methods may be used. For example, the relative flow rates of individual precursor components can be adjusted with mass flow control valves, metering needle valves, or simply by adjusting the temperature of the precursor's container to adjust the vapor pressure of that component. Flow rates can also be affected by using orifices (apertures) of different sized, or by using tubing with different inner diameters. Finally, it is possible to mix multiple precursor chemicals in the same vessel, such that opening a single valve admits a mixture of precursor gases into the instrument's vacuum chamber. Regardless of the delivery strategy used to deliver the multi-component precursor mixture, precursor mixtures can be used to tune the properties of the deposited material layer regardless of the hardware or system for creating the mixture.

Deposition material layers from precursor mixtures can be applied for a variety of different applications. In TEM lamella preparation, tuning the hardness of the sacrificial protective cap can prevent lamella failure due to erosion from the beam tails, and can minimize cross-sectioning artifacts such as curtaining and golf-tee as well as sidewall slope changes at interfaces. Another application for composite material deposition is for use to create single-sided FIB cross-section in general, with a cut face that is free of defects and slope changes.

Figure 15:
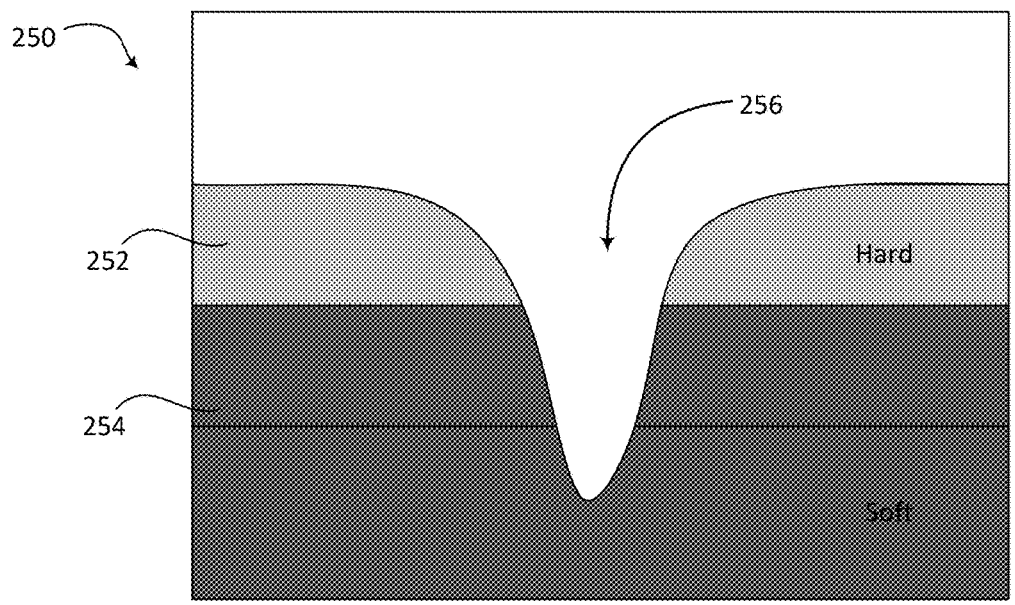
FIG. 15 shows an embodiment of composite material deposition for a substrate having formed vias structures.

Composite deposition layers can also be used to control the milled profile of high-aspect ratio structures (such as vias) that are created with ion beam milling. This may be useful for FIB nano- and micro-fabrication, or for ion-beam lithography techniques. In this application as seen in FIG. 15, a workpiece 250 includes a thin composite deposition capping material 252 deposited onto a substrate 254 into which the user wants to create the high-aspect ratio structure such as via 256. The specific recipe for the composite deposition should be chosen to be "harder" than the underlying target material. As the mill initially progresses, the ion beam will penetrate deeper and deeper into the hard deposition layer 252. Eventually, the mill will reach the interface between the hard deposition 252 and the soft underlying substrate 254. At this point, the underlying substrate 254 will begin to be milled, but only in the center of the ion beam profile, where the milling speed was highest. Because the underlying substrate 254 is softer than the capping material 252, and because the ion beam profile is approximately Gaussian, the soft material 254 should be rapidly milled by the intense center of the ion beam distribution, while the less intense "tails" of the ion beam still have not penetrated the harder capping material 252.

Thus, the arrangement of a harder capping film on top of a softer target material has a sharpening effect on the shape of the ion milling probe, and it is possible to obtain vias with narrower dimensions that would be possible to achieve with an uncapped substrate. If desired, the top capping film could be removed in a final step, leaving the "sharpened" high aspect ratio mills behind. This could be achieved, for example, by using a hard carbon film over a silicon substrate, and the carbon film could be removed with an oxygen plasma cleaning step. Thus, a high aspect ratio structure with relatively narrow dimensions and parallel sidewalls may be formed.

Figure 16:
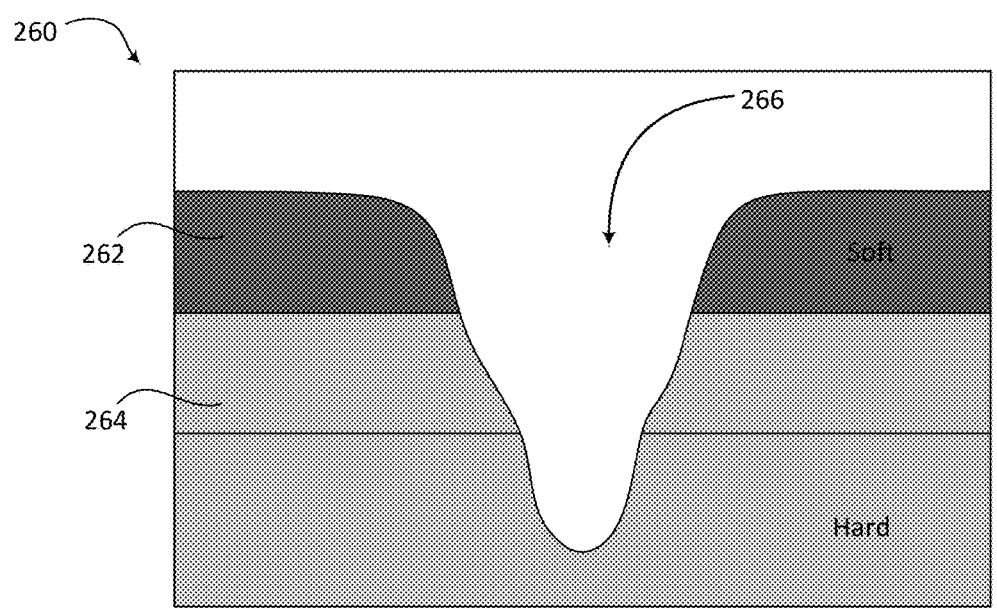
FIG. 16 shows another embodiment of composite material deposition for a substrate having formed vias structures.

In another example, a via with a chamfered or tapered profile (flared open at the top) may be formed by depositing a capping film that is softer than the underlying substrate. In this example seen in FIG. 16, a workpiece 260 is shown with a capping layer 262 that is softer than the underlying substrate 264 formed with a via 266. The effect of the beam tails on the soft capping layer 262 will create more lateral erosion, resulting in a pronounced widening at the top of the via structure, as compared to a via milled without a cap.

Figure 17:
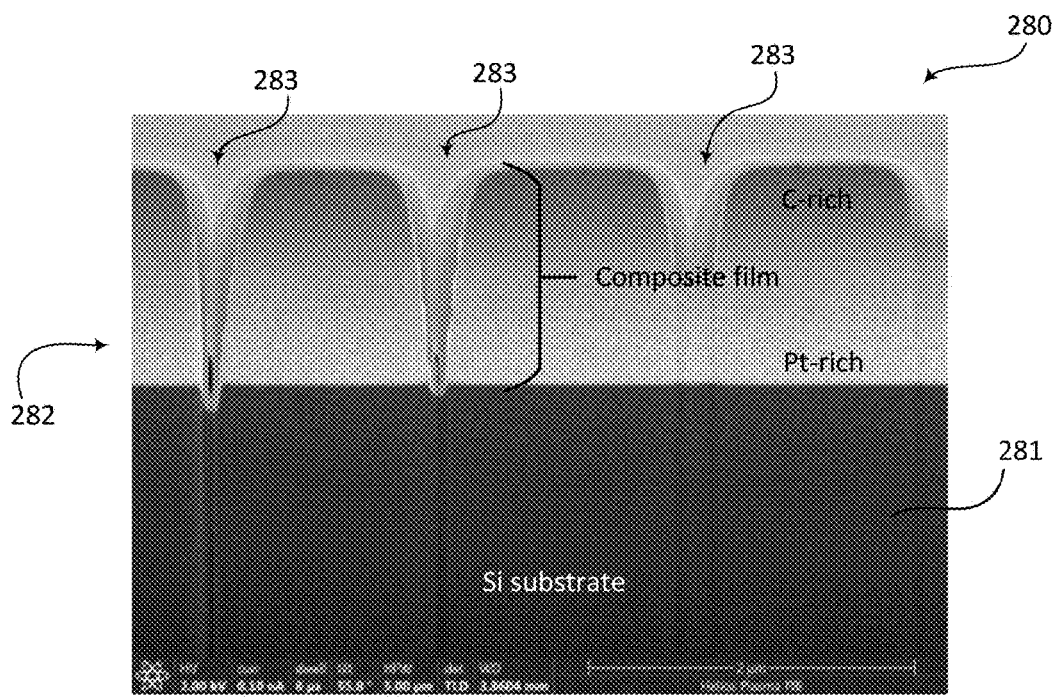
FIG. 17 shows another embodiment of composite material deposition for a substrate having formed vias structures.
Figure 18:
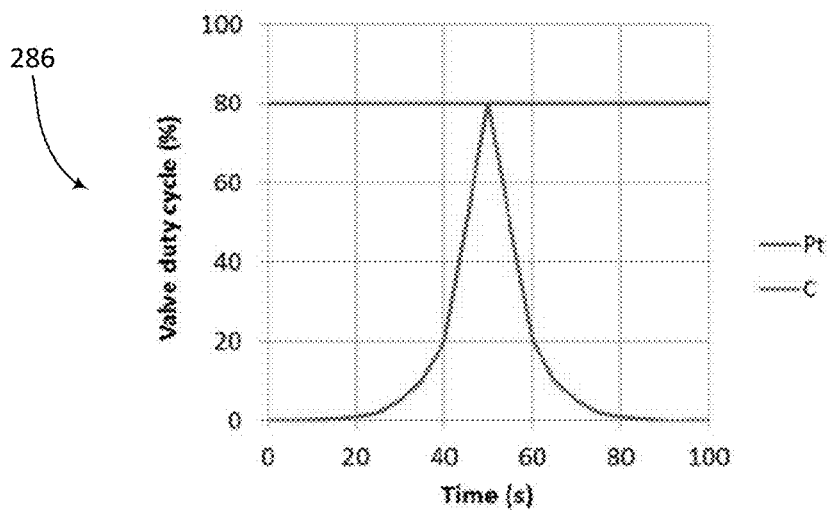
FIG. 18 shows the valve duty cycle for the composite material deposition of FIG. 17.

FIG. 17 shows an embodiment of a workpiece sample 280 with a silicon substrate 281 with a composite layer 282 in which FIB-milled vias 283 are created wherein the composite layer 282 has a "hardness" that varies from bottom to top of the layer. Such a composite layer can be created by adjusting the duty cycle of the individual precursor components during the course of the deposition. For example, a Pt—C composite layer that varies from soft-to-hard (bottom-to-top) could be deposited by beginning the deposition with a Pt-rich mixture, and gradually transitioning to a C-rich mixture as the deposition grows. The valve duty cycle for such a process is shown in FIG. 18 by graph 286.

Figure 19:
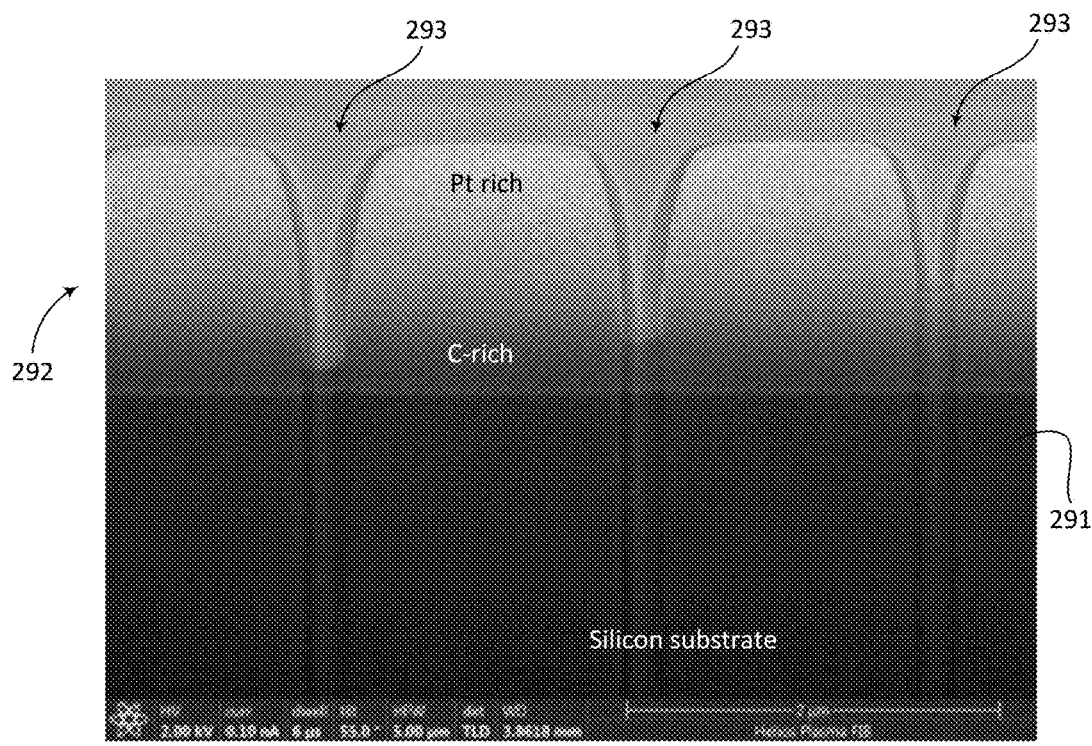
FIG. 19 shows yet another embodiment of composite material deposition for a substrate having formed vias structures.
Figure 20:
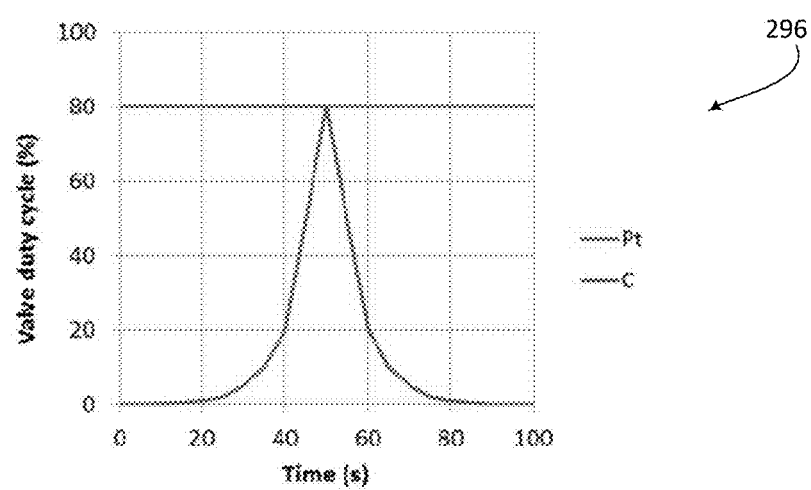
FIG. 20 shows the valve duty cycle for the composite material deposition of FIG. 19.

FIG. 19 shows a reverse process with a workpiece sample with a silicon substrate 291 having a composite layer 292 in which FIB-milled vias 293 are created wherein the composite layer 292 has a "hardness" that varies from bottom to top of the layer. Such a composite layer can be created by adjusting the duty cycle of the individual precursor components during the course of the deposition. For example, a Pt-C composite layer that varies from hard-to-soft (bottom-to-top) could be deposited by beginning the deposition with a C-rich mixture, and gradually transitioning to a Pt-rich mixture as the deposition grows. The valve duty cycle for such a process is shown in FIG. 20 by graph 296.

Although Pt—C mixtures have been discussed as examples of composite layers, it should be understood that other precursor combinations result in deposition layers with variable material properties as well. For example, a carbon-platinum composite may be obtained with precursors of naphthalene and (methylcyclopentadienyl) trimethyl platinum. A carbon-tungsten composite may be obtained using naphthalene and $W(CO)_6$ precursors. Precursors of (methylcyclopentadienyl) trimethyl platinum and $W(CO)_6$ may be used to obtain a platinum-tungsten composite and a carbon-SiOx composite may be obtained with precursors of naphthalene and TEOS or TMCTS or HMCHS.

It is possible to adjust the "hardness" of dielectric depositions, which are typically performed with a siloxane-based precursor and an oxidizer. A high concentration of oxidizing agent will lead to a deposition layer with the fully-saturated $SiO_2$ stoichiometry, whereas a layer deposited with a depleted amount of oxidizer will not be fully saturated, and will have a stoichiometry $SiO_x$, with X<2. Any of the following siloxane-oxidizer combinations is suitable for such tuning: TEOS (tetraethylorthosilicate) and $O_2$; TMCTS (tetramethylcyclotetrasiloxane) with $N_2O$; and HMCHS (hexamethylcyclohexasiloxane) and water. However, any of the siloxanes can be used with any of the oxidizers.

Plasma FIB instruments which generate any of the following primary ions: O+, $O_2^+$, $O_3^+$, $N^+$, $N_2^+$, $H_2O^+$, $H_2O_2^+$, $N_2O^+$, $NO^+$, $NO_2^+$; can potentially be used in conjunction with a siloxane precursor to deposit dielectric layers with variable hardness. In this case the oxidizing agent is the primary beam species itself. Thus, the deposited layers can be made to range from the fully saturated $SiO_2$ stoichiometry to a less-saturated $SiO_x$ (X<2) stoichiometry by adjusting the beam current density, precursor flux, and/or ion beam energy during the deposition process.

It should be understood that although the above examples discuss modulating material "hardness," or resistance to sputtering from an ion beam, other material properties are also adjustable using the same methods. For example, the resistivity of dielectric films will increase with increasing oxidizer concentration. Thus, by controlling the siloxane-oxidizer mixture the user can deposit films with more or less electrical conductivity. The optical transparency of deposited films is another property that can be modulated by precursor mixing. Additionally, material deposition using the disclosed methods may be obtained by laser-assisted precursor decomposition or by thermal decomposition on a heated surface.

According to a second preferred embodiment of the present invention, a substrate, such as a semiconductor wafer, is loaded into a dual-beam FIB/SEM system having both a FIB column and a SEM column. A typical dual-beam system configuration includes an electron column having a vertical axis and an ion column having an axis tilted with respect to the vertical (usually at a tilt of approximately 52 degrees). One such system is the Helios family of Dual-Beam™ Systems, commercially available from FEI Company of Hillsboro, Oreg., the assignee of the present invention.

Figure 21:
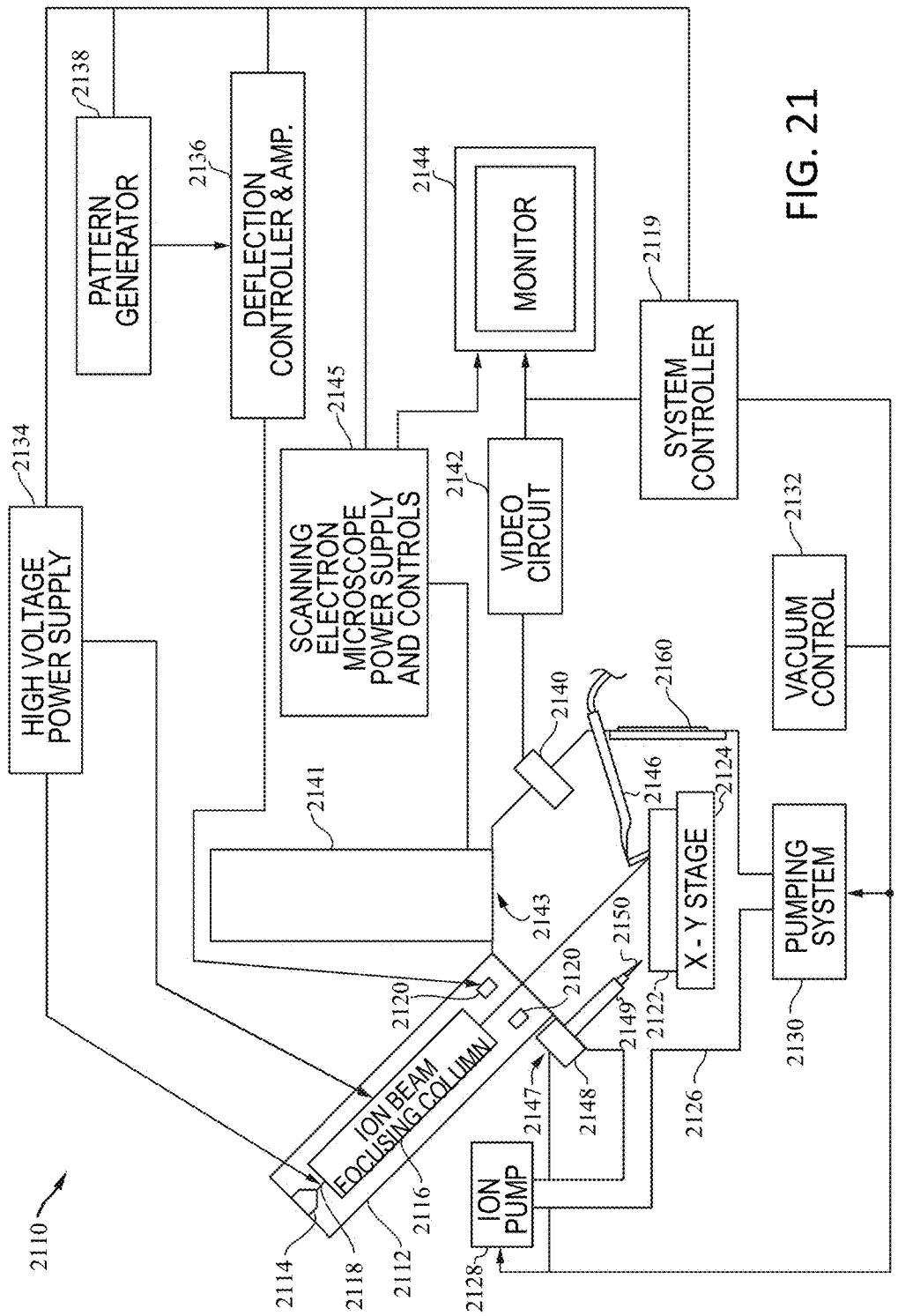
FIG. 21 shows another embodiment using a dual beam system of the type for carrying out the present invention.

FIG. 21 shows a typical dual-beam FIB/SEM system 2110, suitable for practicing the present invention. System 2110 includes an evacuated envelope having an upper neck portion 2112 within which are located a liquid metal ion source 2114 or other ion source and a focusing column 2116. Other types of ion sources, such as multicusp or other plasma sources, and other optical columns, such as shaped beam columns, could also be used, as well as electron beam and laser systems.

An ion beam 2118 passes from liquid metal ion source 2114 through ion beam focusing column 2116 and between electrostatic deflection means schematically indicated at deflection plates 2120 toward a substrate or work piece 2122, which comprises, for example, a semiconductor device positioned on stage 2124 within lower chamber 2126. Stage 2124 can also support one or more TEM sample holders, so that a sample can be extracted from the semiconductor device and moved to a TEM sample holder. Stage 2124 can preferably move in a horizontal plane (X and Y axes) and vertically (Z axis). In some systems, stage 2124 can also tilt approximately sixty (60) degrees and rotate about the Z axis. A system controller 2119 controls the operations of the various parts of FIB system 2110. Through system controller 2119, a user can control ion beam 2118 to be scanned in a desired manner through commands entered into a conventional user interface (not shown). Alternately, system controller 2119 may control FIB system 2110 in accordance with programmed instructions stored in a computer readable memory, such as a RAM, ROM, or magnetic or optical disk. The memory can store instructions for carrying out the methods described above in an automated or semi-automated manner. Images from the SEM can be recognized by the software to decide when to continue processing, when to stop processing, and where to locate the beam for milling.

For example, a user can delineate a region of interest on a display screen using a pointing device, and then the system could automatically perform the steps described below to extract a sample. In some embodiments, FIB system 2110 incorporates image recognition software, such as software commercially available from Cognex Corporation, Natick, Mass., to automatically identify regions of interest, and then the system can manually or automatically extract samples in accordance with the invention. For example, the system could automatically locate similar features on semiconductor wafers including multiple devices, and take samples of those features on different (or the same) devices.

An ion pump 2128 is employed for evacuating upper neck portion 2112. The lower chamber 2126 is evacuated with turbomolecular and mechanical pumping system 2130 under the control of vacuum controller 2132. The vacuum system provides within lower chamber 2126 a vacuum of between approximately $1\times10^{-7}$ Torr ($1.3\times10^{-7}$ mbar) and $5\times10^{-4}$ Torr ($6.7\times10^{-4}$ mbar). For the deposition precursor gas or if an etch-assisting gas or an etch-retarding gas is used, the chamber background pressure may rise, typically to about $1\times10^{-5}$ Torr ($1.3\times10^{-5}$ mbar).

High voltage power supply 2134 is connected to liquid metal ion source 2114 as well as to appropriate electrodes in ion beam focusing column 2116 for forming an approximately 1 keV to 60 keV ion beam 2118 and directing the same toward a sample. Deflection controller and amplifier 2136, operated in accordance with a prescribed pattern provided by pattern generator 2138, is coupled to deflection plates 2120 whereby ion beam 2118 provided by pattern generator 2138, is coupled to deflection plates 2120 whereby ion beam 2118 may be controlled manually or automatically to trace out a corresponding pattern on the upper surface of work piece 2122. In some systems the deflections plates are placed before the final lens, as is well known in the art. Beam blanking electrodes (not shown) within ion beam focusing column 2116 cause ion beam 2118 to impact onto blanking aperture (not shown) instead of target 2122 when a blanking controller (not shown) applies a blanking voltage to the blanking electrode.

The liquid metal ion source 2114 typically provides a metal ion beam of gallium. The source typically is capable of being focused into a sub one-tenth micrometer wide beam at work piece 2122 for either modifying the work piece 2122 by ion milling, enhanced etch, material deposition, or for the purpose of imaging the work piece 2122. If desired, a charged particle detector 2140 can be used for detecting secondary ion or electron emission to be connected to a video circuit 2142 that supplies drive signals to video monitor 2144 and receiving deflection signals from controller 2119.

The location of charged particle detector 2140 within lower chamber 2126 can vary in different embodiments. For example, a charged particle detector 2140 can be coaxial with the ion beam and include a hole for allowing the ion beam to pass. In other embodiments, secondary particles can be collected through a final lens and then diverted off axis for collection. A scanning electron microscope (SEM) 2141, along with its power supply and controls 2145, are optionally provided with the FIB system 2110.

A gas delivery system 2146 extends into lower chamber 2126 for introducing and directing a gaseous vapor toward work piece 2122. U.S. Pat. No. 5,851,413, to Casella et al. for "Gas Delivery Systems for Particle Beam Processing," assigned to the assignee of the present invention, describes a suitable gas delivery system 2146. Another gas delivery system is described in U.S. Pat. No. 5,435,850 to Rasmussen for a "Gas Injection System," also assigned to the assignee of the present intention. For example, iodine can be delivered to enhance etching, or a metal organic compound can be delivered to deposit a metal.

A micromanipulator 2147, such as the EasyLift micromanipulator from FEI, Hillsboro, Oreg., the assignee of the present invention, can precisely move objects within the vacuum chamber. Micromanipulator 2147 may comprise precision electric motors 2148 positioned outside the vacuum chamber to provide X, Y, Z, and theta control of a portion 2149 positioned within the vacuum chamber. The micromanipulator 2147 can be fitted with different end effectors for manipulating small objects. In the embodiments described below, the end effector is a thin probe 2150. The thin probe 2150 may be electrically connected to system controller 2119 to apply an electric charge to the probe 2150 to control the attraction between a sample and the probe.

A door 2160 is opened for inserting work piece 2122 onto X-Y stage 2124, which may be heated or cooled, and also for servicing an internal gas supply reservoir, if one is used. The door is interlocked so that it cannot be opened if the system is under vacuum. In some embodiments, an atmospheric wafer handling system may be utilized. The high voltage power supply provides an appropriate acceleration voltage to electrodes in ion beam focusing column 2116 for energizing and focusing ion beam 2118. When it strikes work piece 2122, material is sputtered, that is physically ejected, from the sample. Alternatively, ion beam 2118 can decompose a precursor gas to deposit a material. Focused ion beam systems are commercially available, for example from FEI Company, Hillsboro, Oreg., the assignee of the present application. While an example of suitable hardware is provided above, the invention is not limited to being implemented in any particular type of hardware.

In this embodiment, material deposition can be carried out by forming a protective capping material of two or more distinct layers. A user may choose to deposit a "softer" material first, to be in direct contact with the underlying substrate, and then a second, "harder" layer may be deposited on top of the first layer. The harder top layer will resist erosion from the ion beam, while the softer bottom layer will prevent cross-sectioning artifacts. In particular, if the bottom layer can be chosen to match the sputter rate of the underlying material, then the risk of cross-sectioning artifacts can be minimized. In other cases, the order may be reversed, with the harder material deposited first, followed by the softer material. This arrangement may be preferred when FIB milling hard materials such as diamond, carbon, or silicon carbide.

Figure 22:
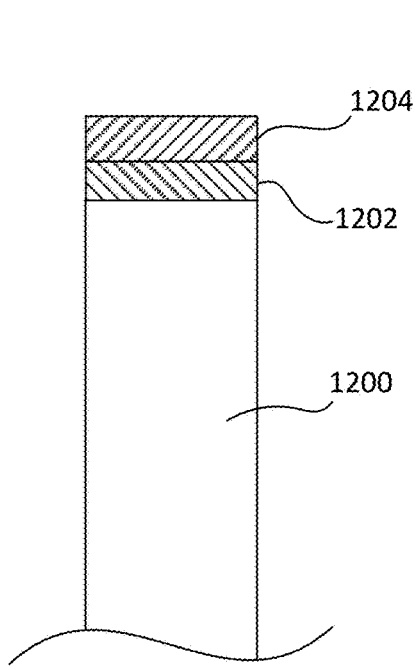
FIG. 22 shows a lamella profile with a protective layer of distinct materials.

For example, as seen in FIG. 22, a lamella substrate 1200 has a protective layer of material having a bottom layer 1202 that is first deposited preferably using electron beam induced deposition (EBID) onto the top surface of substrate 1200 to prevent damage to the upper region of the substrate 1200 near the top surface where the region of interest is generally located. An alternative is to use low energy (<8 keV) IBID, which also results in very low damage to the top surface. In some processes, a low-energy FIB deposition is used rather than an EBID. This first bottom layer material 1202 is chosen to match the etch rate of the material of substrate 1200 as closely as possible, particularly in the <5 kV FIB@10-45 degree off glancing angle operational regime. For silicon (Si)-based samples, this bottom layer 1202 is preferably a type of silicon oxide material such as TEOS (IDEP), TEOS+$H_2O$ (IDEP2), TEOS+$O_2$, HMCHS, HMCHS+$O_2$ (IDEP3), HMCHS/$H_2O$ and HMCHS/$N_2O$, TMCTS, TMCTS+$O_2$, and/or TMCTS/$H_2O$, TMCTS/$N_2O$. A top layer material 1204 is then deposited on top of the bottom layer 1202 using ion beam induced deposition (IBID). The top layer material 1204 is chosen to have a lower etch rate than the material of substrate 1200 to provide protection during the lamella thinning process and to prevent artifacts from forming on the outer surfaces of the sample.

Figure 23:
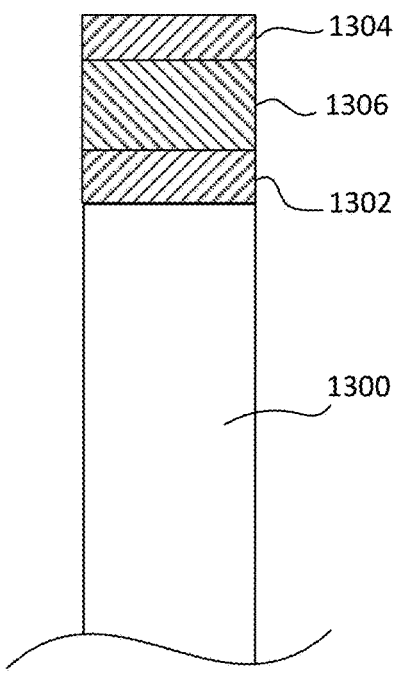
FIG. 23 shows a lamella profile with a protective layer of multiple distinct materials.

More than one top layer may be deposited, if desired. The top layer or layers are preferably tungsten, carbon, or platinum. As an example, carbon has a superior resistance to low-kV FIB milling, which makes for excellent protection, but has significant internal stress which can warp the lamella. Therefore, a pure carbon layer is not desirable. However, as seen in FIG. 23, a substrate 1300 has protective layers including a bottom layer 1302 of material similar to layer 1202 discussed in reference to FIG. 22. A thin layer of carbon 1304 (for example, a 100 nm layer of C after 30 kV processing) on top of a thicker layer of tungsten 1306 (for example, 400 nm or so) would survive low-kV FIB irradiation better than just tungsten alone and the tungsten would provide rigidity to the lamella. In the 35 degree grazing range, which is the angle of the FIB beam to lamella sidewall, the silicon substrate etch rate increases dramatically compared to the tungsten which typically results in golf-tee effects that make the top part of the lamella much thicker than the area a couple hundred nm below the sample surface. A qualitative plot of the angle-dependent sputter rates of silicon and tungsten can be seen in the tables below.

Figure 27A:
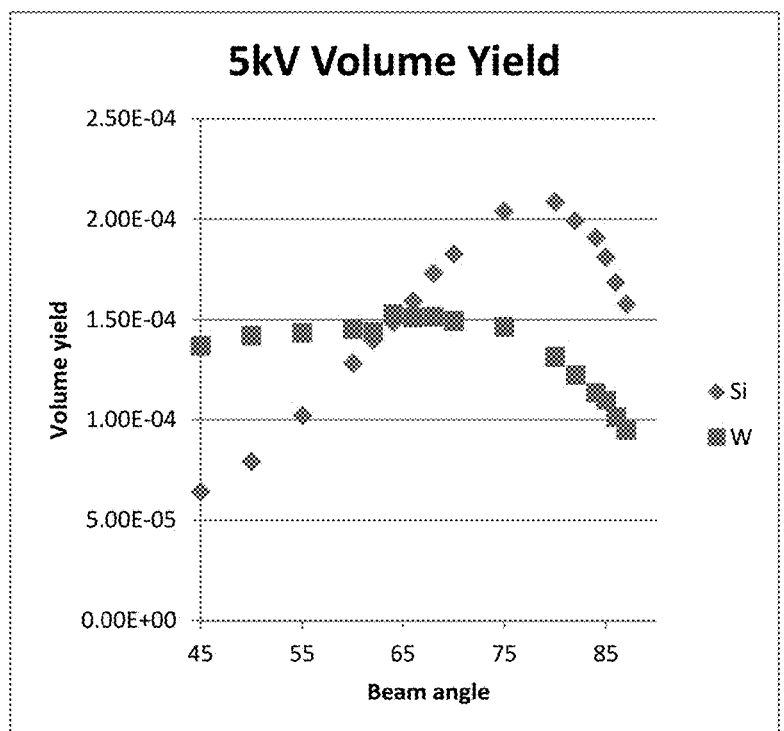
FIGS. 27A and 27B show a plot of the data from Table 1 and 2.
Figure 27B:
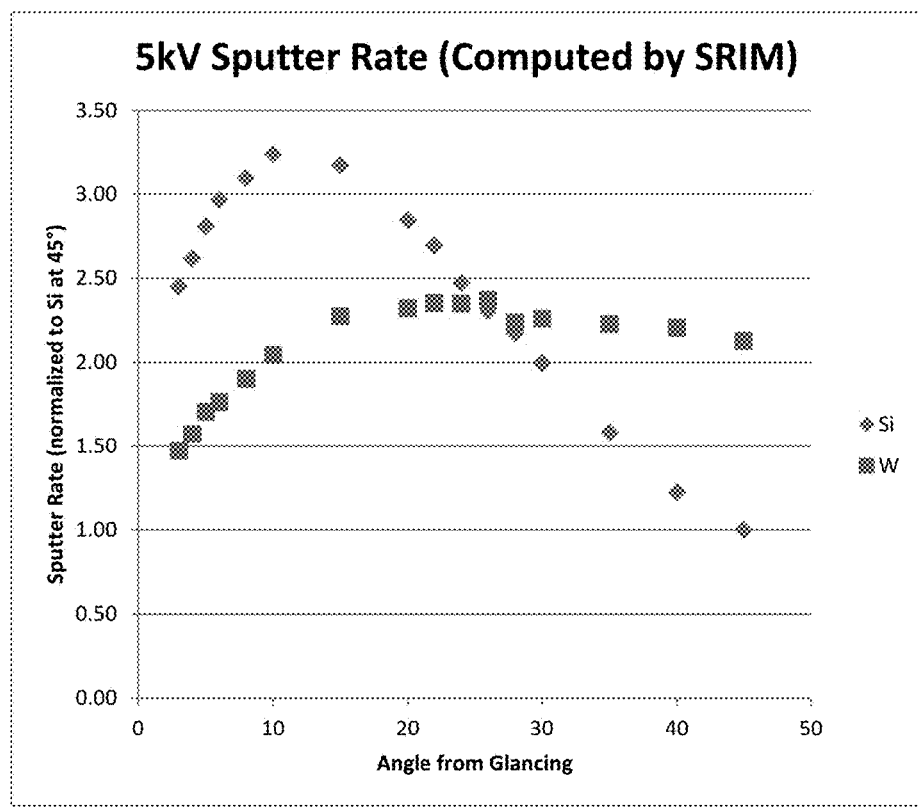

Tables 1 and 2 below shows the sputter and volume yield from 5 kV gallium ions. The data from Tables 1 and 2 are charted in FIGS. 27A and 27B.

TABLE 1

| | Sputter Yield (SRIM) | | Volume Yield, $nm^3$/ion | |
|---|---|---|---|---|
| Angle | Si | W | Si | W |
| 45 | 4.08 | 6.82 | 6.44E−05 | 1.37E−04 |
| 50 | 5.01 | 7.07 | 7.90E−05 | 1.42E−04 |
| 55 | 6.46 | 7.14 | 1.02E−04 | 1.43E−04 |
| 60 | 8.14 | 7.24 | 1.28E−04 | 1.45E−04 |
| 62 | 8.87 | 7.17 | 1.40E−04 | 1.44E−04 |
| 64 | 9.4 | 7.6 | 1.48E−04 | 1.53E−04 |
| 66 | 10.08 | 7.53 | 1.59E−04 | 1.51E−04 |
| 68 | 10.99 | 7.54 | 1.73E−04 | 1.51E−04 |
| 70 | 11.6 | 7.44 | 1.83E−04 | 1.49E−04 |
| 75 | 12.94 | 7.29 | 2.04E−04 | 1.46E−04 |
| 80 | 13.22 | 6.55 | 2.09E−04 | 1.32E−04 |
| 82 | 12.63 | 6.1 | 1.99E−04 | 1.23E−04 |
| 84 | 12.09 | 5.65 | 1.91E−04 | 1.14E−04 |
| 85 | 11.47 | 5.47 | 1.81E−04 | 1.10E−04 |
| 86 | 10.68 | 5.04 | 1.69E−04 | 1.01E−04 |
| 87 | 9.992 | 4.72 | 1.58E−04 | 9.48E−05 |

TABLE 2

| | Sputter rate relative to Si at 45° | |
|---|---|---|
| Angle | Si | W |
| 45 | 1.00 | 2.13 |
| 40 | 1.23 | 2.21 |
| 35 | 1.58 | 2.23 |
| 30 | 2.00 | 2.26 |
| 28 | 2.17 | 2.24 |
| 26 | 2.30 | 2.37 |
| 24 | 2.47 | 2.35 |
| 22 | 2.69 | 2.35 |
| 20 | 2.84 | 2.32 |
| 15 | 3.17 | 2.28 |
| 10 | 3.24 | 2.04 |
| 8 | 3.10 | 1.90 |
| 6 | 2.96 | 1.76 |
| 5 | 2.81 | 1.71 |
| 4 | 2.62 | 1.57 |
| 3 | 2.45 | 1.47 |

In another embodiment of the multilayer deposition strategy, numerous layers may be depositing in an alternating configuration. Stacking multiple layers of different deposition materials can result in a layer that, as an average, has properties intermediate of the two individual components. By adjusting the thicknesses of the individual components, as well as the total number of layers, the user may achieve some degree of tunability, to achieve the desired property of the layer. Typically, the desired film property is intermediate of the individual components. For example, if platinum is too soft and carbon is too hard for a particular application, a multilayer deposition of alternating platinum and carbon depositions may be preferred to a homogeneous layer of either of the individual components.

Figure 24:
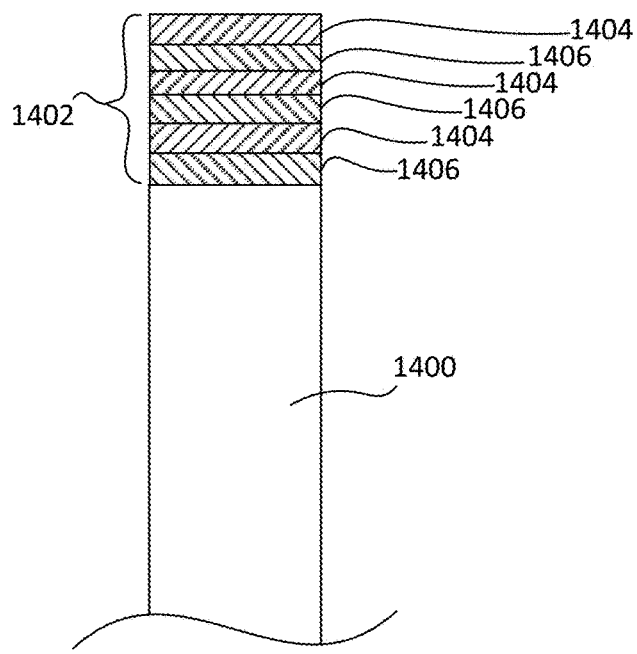
FIG. 24 shows a lamella profile with a protective layer of distinct alternating material.

FIG. 24 shows such an embodiment of material deposition in which substrate 1400 includes a protective layer 1402 with alternating layers of material 1404, 1406 in which the etch rate of the protective layer material 1402 is "tuned" by depositing the alternating, thin layers of material 1404, 1406 using discrete gas chemistries, which forms an alternating "parfait-like" macrostructure with an etch rate that is between the etch rates of the individual components.

Figure 25:
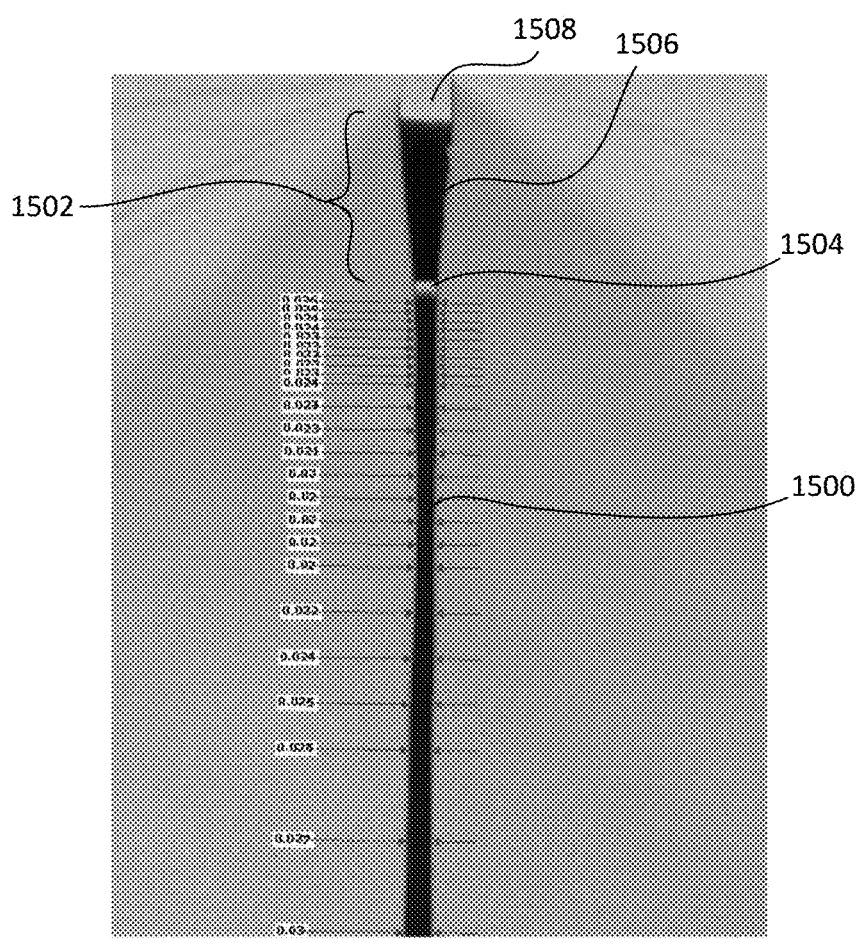
FIG. 25 shows an image of a preferred embodiment of a lamella having multiple protective layers.

FIG. 25 shows an image of a substrate 1500 having a sacrificial protective layer 1502 of discrete layers including a layer of tungsten 1504 for visual observation of the delineation between the top of substrate 1500 and protective layer 1502, a sacrificial layer of SEM deposited silicon oxide 1506 and a top layer 1508 of tungsten. As can be seen, after thinning the "golf tee" effect occurs within the sacrificial protective layer 1502 and not within substrate 1500.

Figure 26:
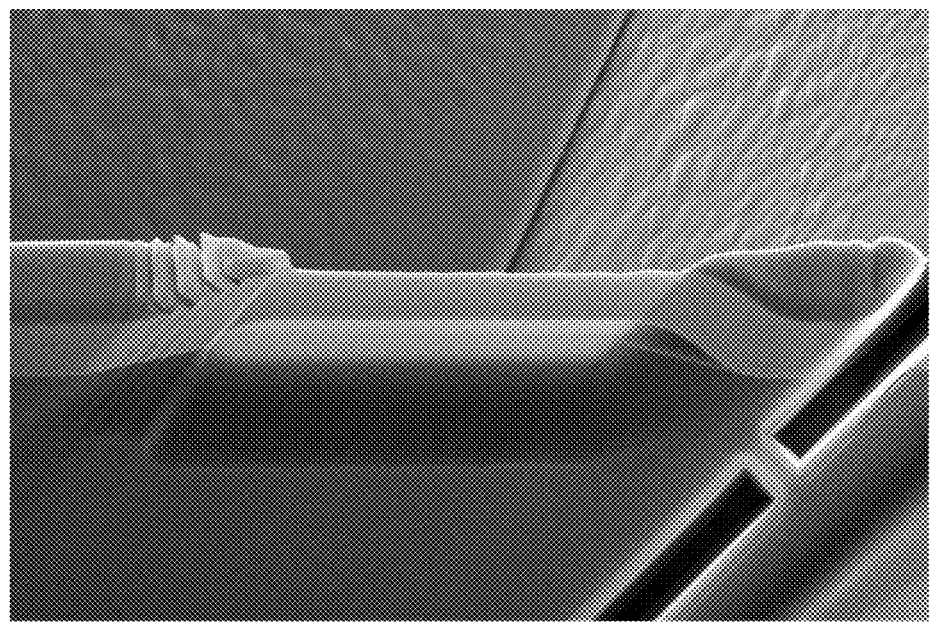
FIG. 26 shows a photomicrograph of another preferred embodiment of a lamella having multiple protective layers.

FIG. 26 shows a silicon lamella with an EBID TEOS layer, an IBID tungsten layer, and an IBID carbon layer.

In the embodiments of FIGS. 12-16, the sacrificial protective layer with similar etch rates to the substrate sample moves the golf-tee up into the protective layer and away from the top of substrate that includes the area of interest for observation and analysis.

Figure 28:
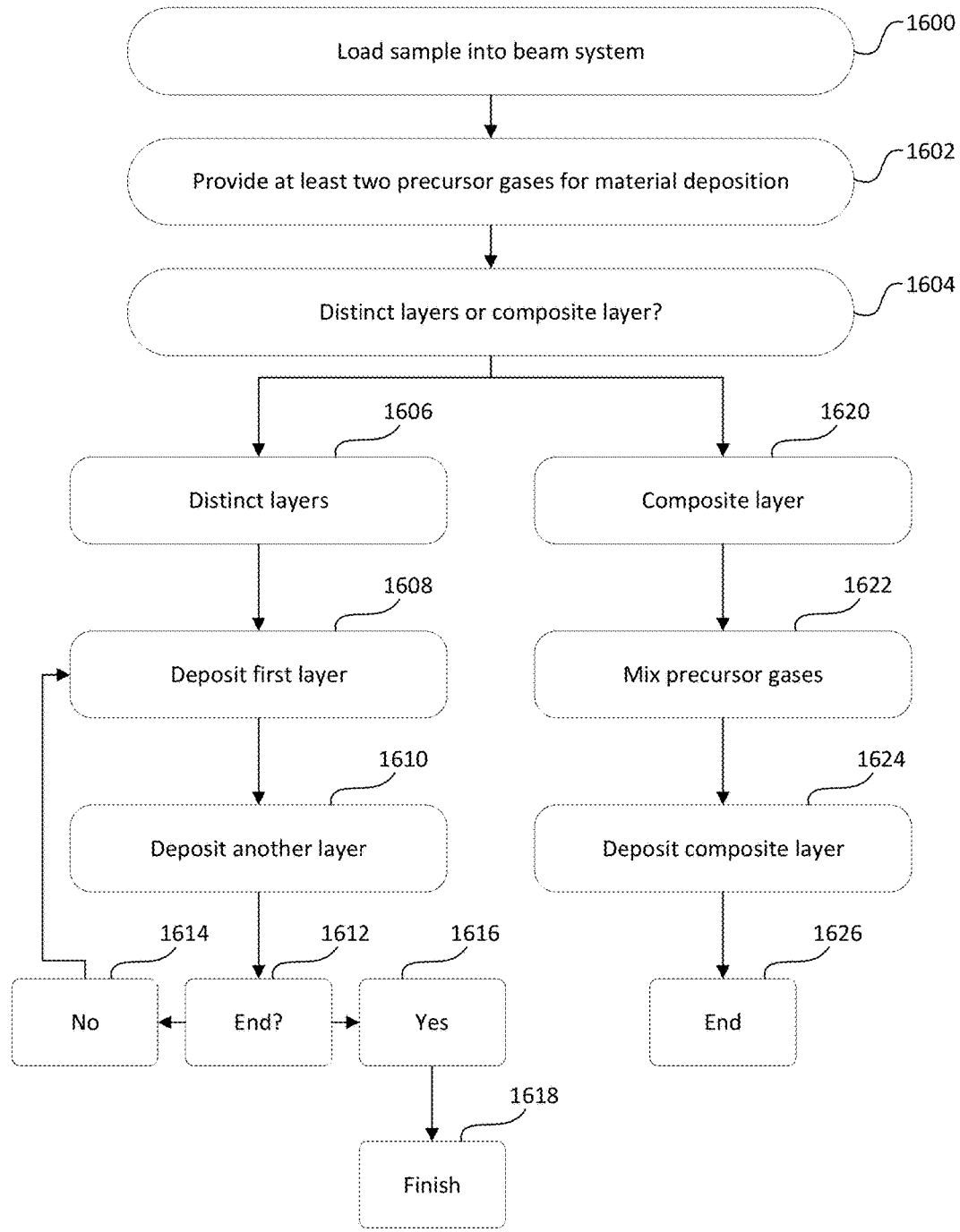
FIG. 28 shows a flow chart for material deposition according to the invention.

As seen in FIG. 28, the present invention provides a method of material deposition in which a sample is loaded into a selected beam system at 1600. At least two precursor gases are provided for material deposition 1602. In decision block 1604 it is determined whether to deposit material in distinct layers or as a composite layer. If distinct layers are deposited 1606, a first layer is deposited on the sample 1608 followed by another layer 1610. If only two layers are to be deposited the decision to end 1612 is determined at 1616 and the process is finished 1618. If more than two layers are to be deposited the decision not to end 1614 is made and the process returns to block 1608 and continues until it is determined to end 1616 and finish the process 1618. If a composite layer is to be deposited 1620 then at least two precursor gases are mixed 1622 according to the determined recipe and the composite layer is deposited 1624 onto the sample and the process is ended 1626.

Some embodiments of the invention provide a method of material deposition onto a sample; comprising, loading a substrate into a charged particle beam system, the substrate containing a region of interest; and directing a charged particle beam toward the substrate to induce deposition from a precursor gas of a protective layer above the region of interest, wherein the sputter rate of the protective layer substantially matches the sputter rate of the substrate.

In some embodiments, the protective layer includes distinctive layers of different material.

In some embodiments, one layer is a silicon oxide deposition.

In some embodiments, one layer is tungsten, carbon, or platinum.

In some embodiments, the protective layer includes alternating layers of material.

In some embodiments, after thinning the sample has opposed faces that are substantially orthogonal below the protective layer.

In some embodiments, the first protective layer has a sputter rate that closely matches the sputter rate of the sample and a second protective layer has a sputter rate that is lower than the sputter rate of the sample.

In some embodiments, the protective layer is a composite mix of material having a sputter rate that substantially matches the sputter rate of the substrate.

Some embodiments of the invention provide an apparatus for material deposition onto a sample, comprising;

an ion beam system including an ion beam source, optics for focusing an ion beam along an axis and onto a substrate, and a micromanipulator for manipulating a sample; and a computer-readable memory storing computer instructions, the instructions including a program for controlling the apparatus and causing the apparatus to carry out the steps of:

loading a substrate into an ion beam system; and directing a charged particle beam toward the substrate to induce deposition from one or more precursor gases to form a protective layer on the sample, the protective layer being composed of at least two materials that have been formulated and arranged according to the material properties of the sample.

Some embodiments provide a method of material deposition onto a sample; comprising:

directing a charged particle beam toward the sample to induce material deposition onto the sample to form a protective layer, wherein the protective layer combines the properties of at least two precursors.

In some embodiments, the protective layer includes alternating layers of different materials.

In some embodiments, the protective layer is a composite mix of different materials.

Although the description of the present invention above is mainly directed at a method of material deposition, the method robust, repeatable and therefore suitable for automation, it should be recognized that an apparatus performing the operation of the method would further be within the scope of the present invention. Although the material deposition methods have been described as being performed with a dual-beam system, it should be understood that the material deposition methods described herein may be performed by a stand-alone SEM system or stand-alone FIB system of any ion polarity. It should be further understood that most beam depositions are not completely pure but may contain "impurities" such as precursor fragments, hydrocarbon incorporation, voids, and density variations that can cause deviations from theoretical models of sputter hardness.

Further, it should be recognized that embodiments of the present invention can be implemented via computer hardware or software, or a combination of both. The methods can be implemented in computer programs using standard programming techniques—including a computer-readable storage medium configured with a computer program, where the storage medium so configured causes a computer to operate in a specific and predefined manner—according to the methods and figures descried in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable. The invention has broad applicability and can provide many benefits as described and shown in the examples above. The embodiments will vary greatly depending upon the specific application, and not every embodiment will provide all of the benefits and meet all of the objectives that are achievable by the invention.

It should be recognized that embodiments of the present invention can be implemented via computer hardware, a combination of both hardware and software, or by computer instructions stored in a non-transitory computer-readable memory. The methods can be implemented in computer programs using standard programming techniques—including a non-transitory computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a non-transitory storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of non-transitory computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

The terms "work piece," "sample," "substrate," and "specimen" are used interchangeably in this application unless otherwise indicated. Further, whenever the terms "automatic," "automated," or similar terms are used herein, those terms will be understood to include manual initiation of the automatic or automated process or step.

In the following discussion and in the claims, the terms "including" and "comprising" are used in an open-ended fashion, and thus should be interpreted to mean "including, but not limited to . . . ." To the extent that any term is not specially defined in this specification, the intent is that the term is to be given its plain and ordinary meaning. The accompanying drawings are intended to aid in understanding the present invention and, unless otherwise indicated, are not drawn to scale. Particle beam systems suitable for carrying out the present invention are commercially available, for example, from FEI Company, the assignee of the present application.

Although the present invention and its advantages have been described in detail, it should be understood that various changes, substitutions and alterations can be made to the embodiments described herein without departing from the scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of charged particle beam processing of a work piece to expose for observation a region of interest, comprising:
   providing, in sequence, flail first, second, and third precursor gases at the work piece;
   directing a charged particle beam toward the work piece to induce deposition of a first protective layer from the first precursor gas on the work piece surface above the region of interest, the first protective layer in direct contact with the work piece surface having a sputter rate equal to the etch rate of the work piece based on first etch parameters;
   directing the charged particle beam toward the work piece to induce deposition of a second protective layer from the second precursor gas, the second protective layer disposed on the first protective layer, and having a sputter rate that is different than the sputter rate of the work piece;
   directing the charged particle beam toward the work piece to induce deposition of a third protective layer from the third precursor gas, the third protective layer disposed on the second protective layer, and having a sputter rate equal to the first protective layer; and
   directing a second charged particle beam toward the work piece to mill through the protective layers to expose the region of interest below the first protective layer.

2. The method of claim 1, in which the first third protective layers comprise silicon oxide.

3. The method of claim 1, in which the second protective layer comprises tungsten, carbon, or platinum.

4. The method of claim 1, further comprising forming a fourth protective layer on the third protective layer, the fourth protective layer being the same as the second protective layer.

5. The method of claim 1, in which directing Hall the second charged particle beam toward the work piece to mill through the protective layers to expose the region of interest below the protective layers comprises producing a lamella having a thickness of less than 100 nm.

6. The method of claim 1, wherein the sputter rate of the second material protective layer is lower than the sputter rate of the work piece.

7. The method of claim 1, wherein
   directing the charged particle beam toward the work piece to induce deposition of the first protective layer from the first precursor gas on the work piece surface above the region of interest comprises directing a focused electron beam toward the work piece; and
   directing the charged particle beam toward the work piece to induce deposition of the second protective layer from the second precursor gas comprises directing a focused ion beam toward the work piece.

8. The method of claim 1 in which:
   directing the charged particle beam toward the work piece to induce deposition of the first protective layer from the first precursor gas comprises directing an electron beam toward the work piece; and
   directing the charged particle beam toward the work piece to induce deposition of the second protective layer from the second precursor gas comprises directing an ion beam toward the work piece.

9. The method of claim 1, in which the second or third protective layer has a sputter rate that is greater than the sputter rate of the work piece.

10. The method of claim 1, in which the second or third protective layer has a sputter rate that is less than the sputter rate of the work piece.

11. A method comprising:
   providing a first precursor gas to a surface of a work piece;
   depositing, in response to a first charged particle beam directed to the surface and interacting with the first precursor gas, a first protective layer on the surface, the first protective layer having an etch rate substantially similar to an etch rate of the work piece based on a first set of etch parameters;

providing a second precursor gas, different from the first precursor gas, to the surface of the work piece;

depositing, in response to a second charged particle beam directed to the surface and interacting with the second precursor gas, a second protective layer on the first protective layer, the second protective layer having an etch rate different than the etch rate of the work piece and the first protective layer based on the first set of etch parameters;

providing the first precursor gas to the surface of the work piece;

depositing, in response to the first charged particle beam directed to the surface and interacting with the first precursor gas, a third protective layer on the second protective layer, the third protective layer having an etch rate substantially similar to the etch rate of the first protective layer based on the first set of etch parameters; and milling a lamella from the work piece that includes at least a portion of the region of interest and further includes a protective cap on at least one end of the lamella comprising the first, second, and third protective layers.

12. The method of claim 11, wherein the first and third protective layers are formed from silicon oxide, and the second protective layer is formed from one of tungsten, carbon, and platinum.

13. The method of claim 11, wherein the first and third protective layers are formed from one of tungsten, carbon, and platinum, and the second protective layer is formed from silicon oxide.

14. The method of claim 11, wherein the first and third protective layers are tungsten and the second protective layer is carbon.

15. The method of claim 11, wherein the first set of etch parameters includes a focused ion beam of less than 5 keV, performed at 10 to 45 degrees off glancing angle.

16. The method of claim 11, wherein the first gas precursor is selected from one of TEOS, TEOS+$H_2O$, TEOS+$O_2$, HMCHS, HMCHS+$O_2$, HMCHS/$H_2O$, HMCHS/$N_2O$, TMCTS, TMCTS+$O_2$, TMCTS/$H_2O$, and TMCTS/$N_2O$.

* * * * *